United States Patent [19]
Conder et al.

[11] Patent Number: 6,071,713
[45] Date of Patent: Jun. 6, 2000

[54] BIOPROCESSES FOR PREPARING 7-ACA AND 7-ADAC

[75] Inventors: Michael J. Conder, Harrisonburg, Va.; John A. Rambosek, Seattle, Wash.; Phyllis C. McAda; Christopher D. Reeves, both of Woodinville, Wash.

[73] Assignee: Gist-Brocades B.V., Netherlands

[21] Appl. No.: 09/340,781

[22] Filed: Jun. 28, 1999

Related U.S. Application Data

[62] Division of application No. 08/839,327, Apr. 17, 1997, Pat. No. 6,017,726, which is a division of application No. 08/439,404, May 11, 1995, Pat. No. 5,629,171, which is a division of application No. 08/250,310, May 27, 1994, Pat. No. 5,559,005, which is a continuation of application No. 07/953,492, Oct. 6, 1992, abandoned, which is a continuation-in-part of application No. 07/777,833, Oct. 15, 1991, abandoned.

[51] Int. Cl.$^7$ ............................. C12P 35/00; C12P 35/02; C12P 35/06; C12N 1/14; C12N 1/20
[52] U.S. Cl. ................................. 435/47; 435/49; 435/51; 435/183; 435/230; 435/243; 435/254.11; 435/252.3; 435/254.5; 435/935; 536/23.1; 536/23.2; 536/23.74

[58] Field of Search .................................. 435/47, 49, 51, 435/183, 230, 243, 254.11, 252.3, 254.5, 935; 536/23.1, 23.2

*Primary Examiner*—Ponnathapu Achutamurthy
*Assistant Examiner*—Tekchand Saidha
*Attorney, Agent, or Firm*—Bierman, Muserlin and Lucas

[57] ABSTRACT

A bioprocess for preparing adipoyl-7-ACA comprising the steps: (a) transforming cells of a strain of *Penicillium chrysogenum* which produces isopenicillin N with an expression vector containing DNA encoding an enzyme, having expandase activity capable of accepting adipoyl 6-APA as a substrate, an enzyme having hydroxylase activity capable of accepting adipoyl-7-ADCA as a substrate and an enzyme having acetyl transferase activity capable of accepting adipoyl 7-ADAC as a substrate; (b) culturing the transformed cells from step a) in a suitable culture medium containing an adipate feedstock, wherein said cells produce adipoyl 6-APA; and (c) culturing the transformed cells producing adipoyl 6-APA of step b) under conditions suitable for expression of said DNA encoding enzyme, thereby producing the end product adipoyl-7-ACA.

3 Claims, No Drawings

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

TCTAGACACC ATGG                                                14

(2) INFORMATION FOR SEQ ID NO:2:

(i) SEQUENCE CHARACTERISTICS:

(A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GTGAGAGTTG ATGGAC                                                           16

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TCTAGACACT ATGGAC                                                           16

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

TCTAGACACC ATGGAC                                                           16

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Asn Ser Gly Ala Val Ala Pro Gly Lys Thr Ala Asn Gly Asn Ala
1               5                   10                  15

Leu Leu Leu Gln Asn Pro
            20

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ser Asn Ser Trp Ala Val Ala Pro Gly Lys Thr Ala Asn Gly Asn Ala
1               5                   10                  15

Leu Leu Leu Gln Asn Pro
            20

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ser Asn Asn Trp Ala Val Ala Pro Gly Arg Thr Ala Thr Gly Arg Pro
1               5                   10                  15
Ile Leu Ala Gly Asp Pro
            20
```

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGAGAGGATC AGTGAGAGTC CATGGACACG ACGG          34

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTTTTGGTGT CGTAGTAGTA CTGAAGGTTC CAG          33

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TACCCGGGGT TCCCGCGAAC T          21

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CATGAAGAAG          10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTCTTCCTAG                                                          10

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTCGGCGCAT CGATGGGTGG AAT                                    23

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCCCACCAT GGCGCCTCAG AT                                     22

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TCTAGCTAGA CACCATGTCG CCTCAGAT                              28

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:16:

GTCGGCGCAT CGATGGGTGG AAT                                    23

(2) INFORMATION FOR SEQ ID NO:17:

(i) SEQUENCE CHARACTERISTICS:

```
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:17:

CTCCGATAGG GCGTGGTACC CGGCCCTACT CTTAT                              35
```

BIOPROCESSES FOR PREPARING 7-ACA AND 7-ADAC

PRIOR APPLICATION

This application is a division of U.S. patent application Ser. No. 839,327 filed Apr. 17, 1997, now U.S. Pat. No. 6,017,726 which is a division of U.S. patent application Ser. No. 439,404 filed May 11, 1995, now U.S. Pat. No. 5,629,171 which is a division of U.S. patent application Ser. No. 250,310 filed May 27, 1994, now U.S. Pat. No. 5,559,005 which is a continuation of U.S. patent application Ser. No. 07/953,492 filed Oct. 6, 1992, now abandoned which is a continuation-in-part of U.S. patent application Ser. No. 07/777,833 filed Oct. 15, 1991, now abandoned.

BACKGROUND OF THE INVENTION

1. Field of the Invention

The present invention is in the field of synthesis methods for the preparation of commercial cephalosporin antibiotics, of which there are presently a significant number, these therapeutic agents now being in their fourth generation. The large variety of side chains to be found in commercial cephalosporins and the significant economic importance of the cephalosporins has placed increased importance on achieving more economic and efficient methods of preparing key intermediates which permit ready synthesis of the various cephalosporins.

One of these key intermediates is 7-aminocephalosporanic acid (7-ACA), which may be represented by the following formula:

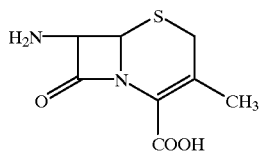

Currently, 7-ACA is produced from Cephalosporin C. Cephalosporin C itself is a fermentation product which is the starting point for nearly all currently marketed cephalosporins. However, synthetic manipulation to produce these various commercial cephalosporins basically starts in most cases with the 7-aminocephalosporanic acid, which must be derived from the Cephalosporin C by cleavage of the 7-aminoadipoyl side chain. Typical commercial cephalosporins derived synthetically from 7-ACA, and which thus have the 3-acetyloxymethylene side chain, include cefotaxime, cephaloglycin, cephalothin, and cephapirin.

Another of the key intermediates is 7-aminodeacetylcephalosporanic acid (7-ADAC), which may be represented by the following formula:

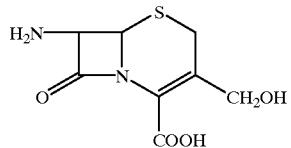

Currently, 7-ADAC is also produced from Cephalosporin C by removal of the 7-D-α-aminoadipoyl side chain, together with conversion of the 3-acetyloxymethyleneside chain to 3-hydroxymethyl. 7-ADAC is a useful intermediate compound in the synthesis of cephalosporins containing modified substituents at the C-3 position.

Currently, the method of choice in the art for cleaving the 7-aminoadipoyl side chain is chemical. The basic iminohalide process requires blocking of the amino and carboxyl groups on the(7-aminoadipoyl side chain, and several methods for accomplishing this are currently used. However, as presently employed, the chemical cleavage process has serious disadvantages. Among these are the requirements of a multi-step and complex process, extremely low operating temperatures, expensive reagents, significant quantities of process by-products resulting in effluent treatment problems, and purification of a highly impure starting material before chemical treatment begins. Consequently, there has been an ongoing search for a microbiological or fermentative process which would achieve enzymatic deacylation of Cephalosporin C to provide 7-aminocephalosporanic acid on a more economic basis than the chemical process currently in use.

However, this search for a successful microbiological process has largely proved futile. This is a result, as is made clear in the literature, of the structure, and especially the stereochemistry, of the-aminoadipoyl side chain of the Cephalosporin C molecule, since penicillin has been successfully deacylated by enzymatic cleavage using penicillin acylase produced by a variety of microorganisms. Reports of successful one-step enzymatic deacylation of Cephalosporin C in the literature, on the otherhand, are often unreproducible or provide only very marginal yields.

Accordingly, the present invention is particularly in the field of preparing the key cephalosporin intermediate 7-ACA, and more particularly, in the field of bioprocesses for the preparation of 7-ACA.

To date, the search for a successful bioprocess for making 7-ACA has largely proved futile, certainly with respect to one of commercial scale. For example, while it has been possible to prepare 6-amino penicillanic acid (6-APA) by direct fermentation and/or by enzymatic treatment of penicillin G, leaving only ring expansion necessary to give 7-ADCA, it has been found that, unfortunately, the Cephalosporium or Streptomyces enzymes which carry out ring expansion in the normal metabolic pathways of these microorganisms do not accept 6-APA as a substrate. These enzymes, which are collectively referred to in the art as the DAOCS or expandase enzyme, are defined As enzymes which catalyze the expansion of penam ring structures found in penicillin-type molecules to ceph-3-em rings, as found in the cephalosporins. Hereafter, these enzymes will be referred to collectively as "the expandase enzyme".

A substrate on which the expandase enzyme does operate is penicillin N, which upon ring expansion and hydroxylation, gives deacetylcephalosporanic acid (DAC). Here, it is only necessary to cleave the (D)-α-aminoadipoyl side chain to give 7-ADAC, but this side chain has proven stubbornly resistant to enzymatic cleavage, giving only unacceptably low yields.

In accordance with the present invention it has been possible to achieve an efficient bioprocess wherein a penicillin compound (having an adipoyl side chain) is produced by a novel fermentation process in high titers, said penicillin compound being an acceptable substrate for the expandase enzyme which is produced in situ by the same microorganism which produces the penicillin compound, having been transformed to express said expandase enzyme. The expandase enzyme then operates to ring expand the penicillin compound to a cephalosporin compound in high yields.

The adipoyl-7-ADCA produced by in situ action of the expandase enzyme has a 3-methyl (—$CH_3$) side lo chain, whereas 7-ACA, the final product, has a 3-acetyloxymethyl

[—CH$_2$OC(O)CH$_3$] side chain. In order to convert the 3-methyl to a 3-acetyloxymethyl side chain, in accordance with the present invention there is also expressed in situ two further enzyme activities in addition to the expandase activity. These are, in order, an hydroxylase and an acetyltransferase, and both are the expression products of genes with which the microorganism producing the penicillin compound has also been transformed. The hydroxylase enzyme converts the 3-methyl side chain of adipoyl-7-ADCA to 3-hydroxymethyl, and the acetyltransferase enzyme converts this 3-hydroxymethyl side chain to the 3-acetyloxymethyl side chain of 7-ACA.

And, importantly in the last critical step of the method of the present invention, the side chain of the penicillin compound, now a cephalosporin compound, is removable by another enzyme system in surprisingly high yields. The unexpected result of this unique, total bioprocess which comprises the present invention, is the production of 7-ACA in surprisingly high yields, and with sufficient economy to represent a reasonable alternative to currently used methods of chemical and biochemical processing.

2. Brief Description of the Prior Art

The novel bioprocess of the present invention provides a unique and surprisingly efficient method for preparing 7-ACA as an economically viable alternative to current chemical synthesis. Continuing efforts in the art to devise such a bioprocess have experienced repeated failure. For example, EP-A-0 422 790 discloses DNA encoding isopenicillin N:acyl-CoA acyltransferase activity of *Aspergillus nidulans* and its use in generating useful cephalosporins in penicillin-producing fungi, which has not heretofore been accomplished in the art. But, this is described as being by way of disruption or displacement of the acyltransferase gene along with addition of genes encoding the epimerase and expandase enzymes from cephalosporin-producing organisms; moreover, no useful transformation and expression result is actually achieved, apparently. Furthermore, had transformation been successful, it still would not have been useful for the purposes of the present invention, since the problem of how to remove the D-α-aminoadipoyl side chain would still remain. Such a failed attempt in the art to obtain significant results in producing commercial cephalosporin intermediates from penicillin-producing fungi cultures is in complete contrast to the results achieved with the method of the present invention.

The first enzymatic bioprocess step in the method of the present invention is ring expansion of adipoyl-6-APA, carried out by an expandase enzyme which is the expression product of an expandase gene with which the non-recombinant *P. chryaogenum* host as been transformed. The use of synch an expandase enzyme has been explored in the prior art. For example, Cantwell et al., in *Curr Genet* (1990) 17:213–221, have proposed a bioprocess for preparing 7-ADCA by ring expansion of penicillin V followed by enzymatic hydrolysis of the resulting deacetoxycephalosporin V to form 7-ADCA. This proposal is based on the availability of a cloned penicillin N expandase gene (cefE) from *S. clavuligerus*: Kovacevic et al., *J. Bacteriol.* (1989) 171:754–760; and Ingolia et al. U.S. Pat. No. 5,070,020. However, since the expandase operates on penicillin N, its natural substrate, but not on penicillin V, the proposal requires genetic engineering to produce a modified expandase gene which can ring-expand the penicillin V. The required modification was not achieved by Cantwell et al., however, and they only succeeded in transforming *Penicillium chrysogenum* with the cef E gene from *Streptomyces clavuligerus* and getting low-level expression of the DAOCS (expandase) enzyme.

The expandase enzyme has been well studied in the art, both with respect to its activity and its genetic sequence. For example, in Wolfe U.S. Pat. Nos. 4,510,246 and 4,536,476, cyclase, epimerase and ring expansion enzymes were isolated separately from a cell free extract of prokaryotic β-lactam producing organisms, including *Streptomyces clavuligerus*, to provide stable enzyme reagents. Dotzlaf U.S. Pat. No. 5,082,772 (EP-A-0 366 354) describes an isolated and purified expandase enzyme from *S. clavuligerus* which is characterized, including by a terminal residue and amino acid composition, and is said to have a molecular weight of about 34,600 Daltons. This is in contrast, however, to the molecular weight of 29,000 assigned to what would appear to be the same enzyme in U.S. Pat. No. 4,536,476. EP-A-0 233 715 discloses isolation and endonuclease restriction map characterization of the expandase gene obtained from *S. clavuligerus* and expression of recombinant expandase-encoding DNA (yielding active expandase enzyme) in an *S. clavuligerus* strain lacking the capability of cephalosporin production. Ingolia et al. U.S. Pat. No. 5,070,020 (EP-A-0 341 892) discloses the DNA sequence encoding the expandase enzyme obtained from *S. clavuligerus* and describes the transformation of a *P. chrysogenum* strain with an expression vector containing said DNA sequence, thereby obtaining expression of the expandase enzyme. While it is suggested that this enzyme is useful for the expansion of substrates other than penicillin N, there is no actual demonstration of such an expansion.

The work described above has focused on the expandase enzyme derived from prokaryotic *S. clavuligerus*. An enzyme apparently having the same ring expansion activity is also expressed by strains of eukaryotic *Cephalosporium acremonium* (also referred to as *Acremonium chrysogenum*). However, in such strains expandase activity is expressed by a bifunctional gene (cefEF), which also expresses the DACS (hydroxylase) activity whose natural function is to convert the desacetoxycephalosporanic acid (DAOC) product of the expandase enzyme to deacetyl cephalosporin C (DAC). The result of this expression is a single, but bifunctional expandase/hydroxylase enzyme. While there have been efforts to separate the activities of these two gene products, none have yet been successful. For example, EP-A-0 281 391 discloses the isolation and DNA sequence identification of the DAOCS/DAOS gene obtained from *C. acremonium* ATCC 11550 together with the corresponding amino acid sequence of the enzyme. A Penicillium is transformed and expresses the enzymes, however, the attempted conversion of penicillins G and V to the corresponding cephalosporins is never demonstrated. Further, despite a suggestion that genetic engineering techniques provide a ready means to separate the genetic information encoding DAOCS from DAGS and separately express them, no actual demonstration of such separation is set forth.

The DAOCS/DACS (expandase/hydroxylase) enzyme of *C. acremonium* has also been well studied in the art, both with respect to its activity and its characteristics and genetic sequence. For example, in Demain U.S. Pat. Nos. 4,178,210; 4,248,966; and 4,307,192 various penicillin-type starting materials are treated with a cell-free extract of *C. acremonium* which epimerizes and expands the ring to give a cephalosporin antibiotic product. Wu-Kuang Yeh U.S. Pat. No. 4,753,881 describes the *C. acremonium* enzyme in terms of its isoelectric point, molecular weights, amino acid residues, ratio of hydroxylase to expandase activities and peptide fragments.

The acetyltransferase enzyme of *C. acremonium* has also been described in the art, with respect to its activity, characteristics, restriction mapping, and nucleotide and amino acid sequences. For example, see EP-A-0 437 378 and EP-A-0 450 758.

The prior art discussed above deals with only a single aspect of the present invention, i.e., the transformation of a *P. chrysogenum* strain with genes expressing the expandase and expandase/hydroxylase enzymes and obtaining expression of those enzymes. The art, however, has only used the expressed enzymes to ring-expand penicillin N, not penicillins G and V. Even in that case, penicillin N has a 7-position side chain which cannot be cleaved enzymatically to leave a free amino group. The present invention is based on the surprising discovery that an adipoyl side chain can be efficiently added by a *P. chrysogenum* strain, that the expandase enzyme expressed in situ can use that compound efficiently as a substrate for ring expansion to adipoyl 7-ADCA, that hydroxylase and acetyltransferase enzymes also expressed La situ can use the adipoyl-7-ADCA as a substrate to produce the 3-acetoxymethyl side chain of 7-ACA, and that the adipoyl side chain can then be efficiently removed by yet another enzyme to give 7-ACA. While various isolated fragments of the present invention may be found in the prior art, there has been no suggestion that they be combined to give the unexpected results obtained with the method of the present invention.

For example, production of 6-adipoyl penicillanic acid is known in the art; see Ballio, A. et al., *Nature* (1960) 185, 97–99. The enzymatic expansion of 6-adipoyl penicillanic acid, but only on an in vitro basis, is also known in the art; see Baldwin et al., *Tetrahedron* (1987) 43, 3009–3014; and EP-A-0 268 343. And, enzymatic cleavage of adipoyl side chains is also known in the art; see for example, Matsuda et al., *J. Bact.* (1987) 169, 5815–5820.

The adipoyl side chain has the following structure: COOH—$(CH_2)_4$—CO—, while two side chains of closely related structure are those of glutaryl, having the following formula: COOH—$(CH_2)_3$—CO—, and of (D)-α-aminoadipoyl, having the formula: COOH—$CH(NH_2)$—$(CH_2)_3$—CO—. The enzymatic cleavage of glutaryl side chains is known in the art. See, e.g., Shibuya et al., *Agric. Biol. Chem.* (1981) 45, 1561–1567, and U.S. Pat. No. 3,960,662; Matsuda and Komatsu, *J. Bact.* (1985) 163, 1222–1228; Matsuda et al., *J. Bact.* (1987) 169, 5815–5820; Jap. 53-086084 (1978—Banyu Pharmaceutical Co. Ltd.); and Jap. 52-128293 (1977—Banyu Pharmaceutical Co. Ltd.). Also, EPA-A-0 453 048 describes methods for improving the adipoyl-cleaving activity of the glutaryl acylase produced by Pseudomonas SY-77-1. By substituting different amino acids at certain locations within the alpha-subunit, a three to five times higher rate of adipoyl cleavage (from adipoyl-serine) was observed. It should be noted that although FP-A-0 453 048, apparently, demonstrates an acylase with improved activity towards adipoyl-side chains, it does not describe any ways (either chemical or through a bioprocess in any way analogous to that described in the instant specification) in which an adipoyl-cephalosporin might be generated in the first place.

Where a (D)-α-aminoadipoyl side chain is present, it is known in the art to first enzymatically remove the amino group and shorten the side chain with a (D)-amino acid oxidase, leaving a glutaryl (GL-7) side chain, with removal of the glutaryl side chain by a second enzyme (glutaryl acylase). Such a two-step cleavage is disclosed in Matsuda U.S. Pat. No. 3,960,662; EP-A-0 275 901; Jap. 61-218057 (1988—Komatsu, Asahi Chemical Industry Co.); WO 90/12110 (1990—Wong, Biopure Corp.); and EP-A-0 436 355, Isogai et al., also *Bio/Technology* (1991) 9, 188–191.

It is also known in the art to carry out one-step cleavage of the (D)-α-aminoadipoyl side chain, particularly using recombinant techniques. See, e.g.:

One-step (D)-α-aminoadipoyl side chain cleavage:

Jap. 53-94093 (Meiji, Pseudomonas sp. BN-188);

Jap. 52-143289 (=U.S. Pat. No. 4,141,790, Meiji, Aspergillus sp.);

U.S. Pat. No. 4,774,179 (Asahi 1988, Pseudomonas sp. SE-83 and SE-495), =Jap. 61-21097 and Jap. 61-152286;

Fr. Pat. 2,241,557 (Aries 1975, *Bacillus cereus* var. fluorescens);

Jap. 52-082791 (Toyo Jozo 1977, *Bacillus megaterium* NRRL B 5385);

EP-A-0 321 849 (Hoechst, Pseudomonas, *Bacillus subtilis*, γ-glutamyl transpeptidase);

EP-A-0 322 032, EP-A-0 405 846, and U.S. Pat. No. 5,104,800 (Merck, *Bacillus megaterium*);

EP-A-0 283 218 and U.S. Pat. No. 4,981,789 (Merck, *Arthrobacter viscosus*);

One-Step-Recombinant: Ceph C→7-ACA:

Jap. 60-110292 (Asahi 1985, Comamonas, recombinant *E. coli* with gene from Comamonas sp. SY-77-1, one-step conversion);

Jap. 61-152-286 (Asahi 1986, Pseudomonas, recombinant *E. coli* with gene from Pseudomonas sp. SE83, genetic sequences described and claimed, one step process already claimed in U.S. Pat. No. 4,774,179);

Jap. 63-74488 (Asahi 1988, *Trigonopsis variabilis*, Comamonas, recombinant *E. coli* expression of D-amino acid oxidase and GL-7-ACA acylase construct).

EP-A-0 475 652 (Fujisawa, cephalosporin C acylase and its production via recombinant technology).

Various aspects of methods for producing 7-ADAC are known in the art. For example, see U.S. Pat. Nos. 3,304,236 and 3,972,774 (Eli Lilly & Co.); EP-A-0 454 478 (Shionogi & Co., Ltd.); and published Japanese application 04 53,499 (Shionogi & Co., Ltd.).

Reference to Copending Application

Reference is made to copending application Ser. No. 07/933,469, filed Aug. 28, 1992 (Attorney Docket No. 18532IA), which discloses a bioprocess for making 7-ADCA that relies on expression of the activity of the expandase enzyme in a *P. chrysogenum* transformant in the same manner as the bioprocess for making 7-ADAC and 7-ACA described herein. However, in the present bioprocess, additional transformations are utilized for the expression of additional enzymatic activities, in order to achieve a wholly different recombinant metabolic pathway to distinct final products, none of which is suggested in the copending application.

In order to facilitate a better understanding of the method of the present invention and the teachings of the prior art references discussed above, set out immediately below is a representation of the various stages in the metabolic pathways leading to adipoyl-6-APA, adipoyl-7-ADCA, adipoyl-7-ACA, and 7-ACA, the intermediate products, and the enzymes which carry out the transformations involved.

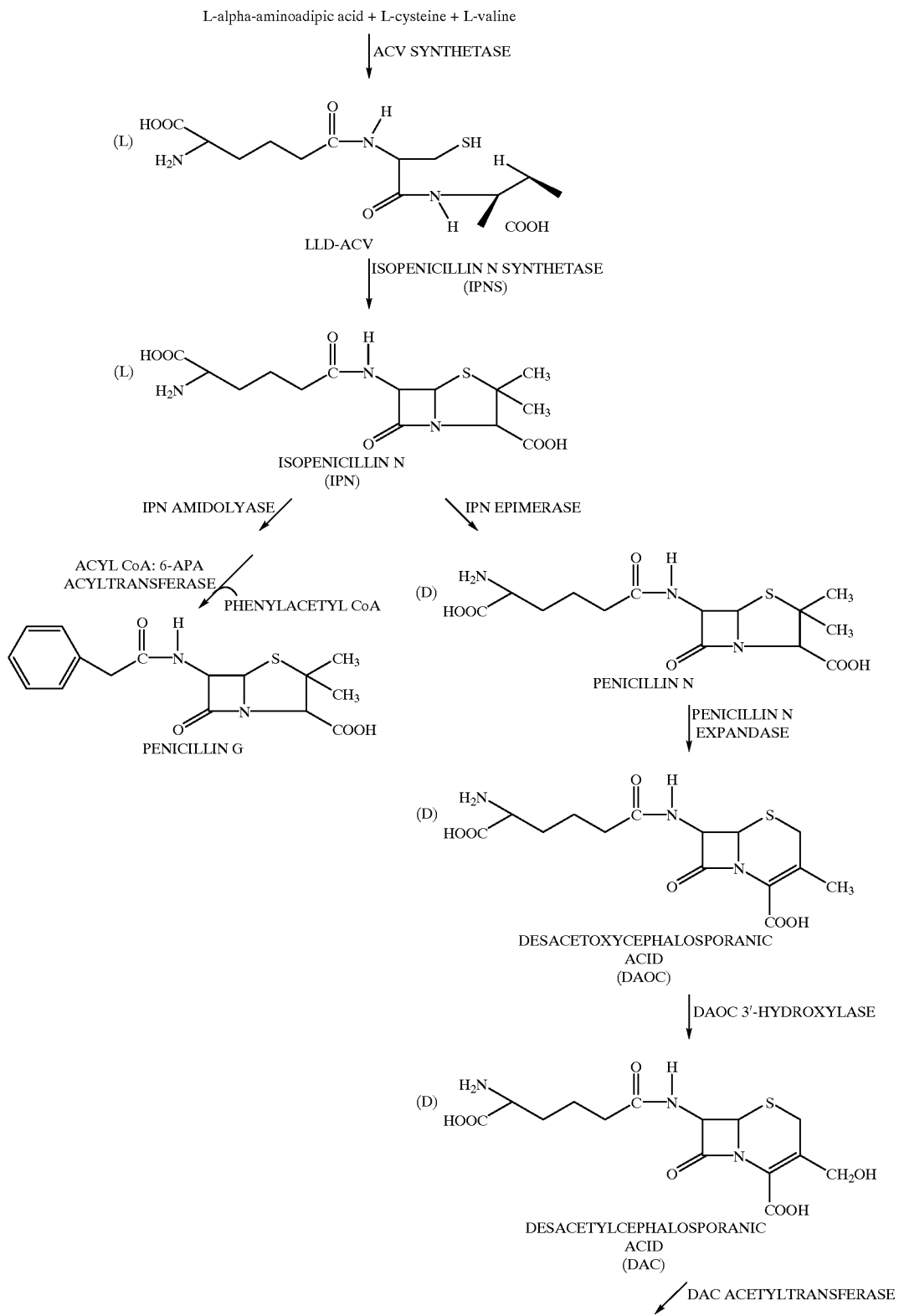

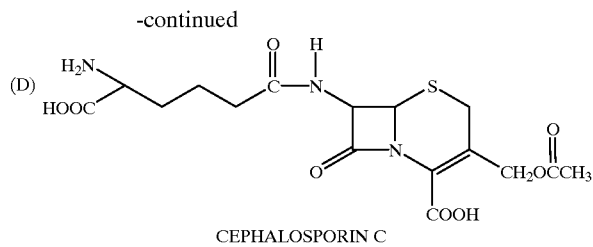

CEPHALOSPORIN C

SUMMARY OF THE INVENTION

The present invention relates to a novel bioprocess for preparing 7-aminodeacetylcephalo-sporanic acid (7-ADAC) comprising the steps of 1) maintaining in a culture medium capable of sustaining its growth, a strain of Penicillium chrysogenum which produces isopenicillin N and adding to said culture medium an adipate feedstock comprising any one or more of adipic acid, or its salts and esters which are capable of being assimilated and utilized by said strain of *Penicillium chrysogenum* to produce adipoyl-6-aminopenicillanic acid (adipoyl-6-APA), whereby said adipoyl-6-APA is produced;

2) carrying out the following enzymatic conversions by in situ expression of the corresponding gene:
   a) adipoyl-6-APA is in rite ring-expanded to form adipoyl-7-aminodesacetoxycephalosporanic acid (adipoyl-7-ADCA) by expandase enzyme wherein said strain of *P. chrysogenum* has been transformed by DNA encoding the activity of the expandase enzyme capable of accepting said adipoyl-6-APA as a substrate, whereupon as a result of its expression, said adipoyl-6-APA produced by said strain is also thereafter in situ ring-expanded to form adipoyl-7-ADCA;
   b) the 3-methyl side chain of adipoyl-7-ADCA is in situ hydroxylated to yield adipoyl-7-aminodeacetylcephalosporanic acid (adipoyl-7-ADAC) by hydroxylase enzyme, wherein said strain of *P. chrysogenum* has been transformed by DNA encoding the activity of the hydroxylase enzyme capable of accepting said adipoyl-7-ADCA as a substrate, whereupon as a result of its expression, said adipoyl-7-ADCA produced by said strain is also thereafter in situ hydroxylated to form adipoyl-7-ADAC; and 3) contacting said adipoyl-7-ADAC with an adipoyl amidase whereby the adipoyl side chain is removed and the 7-ADAC product is formed; and said product is then isolated.

The present invention further relates to a novel bioprocess for preparing 7-aminocephalosporanic acid (7-ACA) comprising the steps of 1) maintaining in a culture medium capable of sustaining its growth, a strain of *Penicillium chrysogenum* which produces isopenicillin N and adding to said culture medium an adipate feedstock comprising any one or more of adipic acid, or its salts and esters which are capable of being assimilated and utilized by said strain of *Penicillium chrysogenum* to produce. adipoyl-6-aminopenicillanic acid (adipoyl-6-APA), whereby said adipoyl-6-APA is produced;

2) carrying out the following enzymatic conversions by in situ expression of the corresponding gene:
   a) adipoyl-6-APA is in situ ring-expanded to form adipoyl-7-aminodesacetoxycephalosporanic acid (adipoyl-7-ADCA) by expandase enzyme wherein said strain of *P. chrysogenum* has been transformed by DNA encoding the activity of the expandase enzyme capable of accepting said adipoyl-6-APA as a substrate, whereupon as a result of its expression, said adipoyl-6-APA produced by said strain is also thereafter in situ ring-expanded to form adipoyl-7-ADCA;
   b) the 3-methyl side chain of adipoyl-7-ADCA is in situ hydroxylated to yield adipoyl-7-aminodeacetylcephalosporanic acid (adipoyl-7-ADAC) by hydroxylase enzyme, wherein said strain of *P. chrysogenum* has been transformed by DNA encoding the activity of the hydroxylase enzyme capable of accepting said adipoyl-7-ADCA as a substrate, whereupon as a result of its expression, said adipoyl-7-ADCA produced by said strain is also thereafter in sit hydroxylated to form adipoyl-7-ADAC; and
   c) adipoyl-7-ADAC is in situ acetylated to yield adipoyl-7-aminocephalosporanic acid (adipoyl-7-ACA), by acetyltransferase enzyme, wherein said strain of *P. chrysogenum* has been transformed by DNA encoding the activity of the acetyltransferase enzyme capable of accepting said adipoyl-7-ADAC as a subs-rate, whereupon as a result of its expression, said adipoyl-7-ADAC produced by said strain is also thereafter in situ acetylated to form adipoyl-7-ACA; and 3) contacting said adipoyl-7-ACA with an adipoyl amidase whereby the adipoyl side chain is removed and the 7-ACA product is formed; and said product is then isolated.

As used herein, the following terms have the indicated meanings:

"7-ACA" means 3-[(acetoyloxy)-methyl]-7-amino-8-oxo-5-thia-1-azabicyclo[4.2.0]oct-2-ene-2-carboxylic acid;

"adipoyl-6-APA" means [2S-(2α, 5α, 6β)]-3,3-dimethyl-7-oxo-6-[hexane-1,6-dioyl) amino]-4-thia-1-azabicyclo[3.2.0]heptane-2-carboxylic acid;

"adipoyl-7-ADCA" means 3-methyl-7-[(hexane-1,6-dioyl)amino]-3-methyl-8-oxo-5-thia-1-azabicyclo[4.2.0]oct-2-ene-2-carboxylic acid; and "adipoyl-7-ADAC" means 3-hydroxymethyl-7-[(hexane-1,6-dioyl)amino]-3-methyl-8-oxo-5-thia-1-azabicyclo[4.2.0]oct-2-ene-2-carboxylic acid.

In particular, the present invention relates to the novel bioprocesses for preparing 7-aminodeacetyl-cephalosporanic acid (7-ADAC) and 7-aminocephalosporanic acid (7-ACA) recited above in which the adipate feedstock is disodium adipate, in which the DNA encoding the activity of the expandase enzyme, hydroxylase enzyme, and acetyltransferase enzyme are all derived from *Cephalosporium acremonium,* and in which the adipoyl acylase is derived from Pseudomonas species.

The present invention further relates to recombinant DNA expression vectors comprising the DNA encoding the activity of the expandase, hydroxylase and acetyltransferase enzymes derived from *Cephalosporium acremonium,* and promoters which drive expression of genes encoding for said enzymes comprising plasmids pPEN/CEPH-1, pPENCACT and pTS-8, as hereinafter described.

The present invention further relates to *Penicillium chrysogenum* host cells transformed with recombinant DNA expression vectors comprising the DNA encoding the activity of the expandase, hydroxylase and acetyltransferase enzymes derived from *Cephalosporium acremonium,* and a promoter which drives expression of said enzyme-encoding DNA comprising the promoter of the *Penicillium chrysogenum* IPNS gene. In particular, the present invention relates to *Penicillium chrysogenum* host cells transformed with recombinant DNA expression vectors comprising plasmids pPEN/CEPH-1, pPenCACT and pTS-8, as hereinafter described.

The present invention still further relates to a method for culturing recombinant *Penicillium chrysogenum* host cells under conditions suitable for gene expression, wherein said recombinant host cells comprise recombinant DNA expression vectors comprising the DNA encoding the activity of the expandase, hydroxylase and acetyltransferase enzymes derived from *Cephalosporium acremonium,* and a promoter which drives expression of said enzyme-encoding DNA comprising the promoter of the *Penicillium chrysogenum* IPNS gene. In particular, the present invention relates to a method of culturing recombinant *Penicillium chrysogenum* host cells under conditions suitable for gene expression, wherein said recombinant host cells comprise recombinant DNA expression vectors comprising plasmids pPEN/CEPH-1, pPenCACT and pTS-8, as hereinafter described.

DETAILED DESCRIPTION OF THE INVTION

The primary aspect of the present invention is a novel bioprocess for preparing 7-aminocephalosporanic acid (7-ACA) and 7-aminodeacetylcephalosporanic acid (7-ADAC), key intermediates in the preparation of synthetic commercial cephalosporins, which may be represented by the following structural formulae:

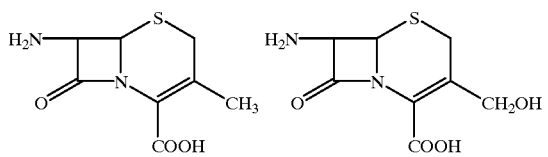

In addition to the cephalosporin nucleus, the distinctive features of 7-ACA are the 7-amino group and the 3-acetyloxymethyl (or 3-acetoxymethyl, as it is more frequently referred to) group. The 7-amino group is one which may be converted to any number of derivative side chains, and thus forms the basis for synthesizing various commercial cephalosporins. The 3-acetyloxymethyl group will often be converted to some other side chain in order to synthesize a commercial cephalosporin.

The 7-ACA final product and adipoyl-7-ACA intermediate product of the method of the present invention may be contrasted with cephalosporin C, another key cephalosporin intermediate which may be represented by the following structural formula:

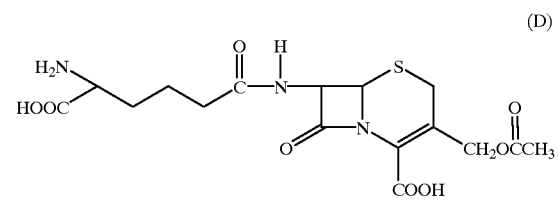

For this intermediate, the 7-(D)-α-aminoadipoyl side chain is not acceptable for further synthetic derivation, and must be cleaved to give the acceptable 7-amino group. Unfortunately, the 7-(D)-α-aminoadipoyl side chain has always proven difficult to remove, whether by chemical or biochemical means.

Definitions

As used in the instant specification, and particularly in the section entitled Description of Preferred Embodiments, the following terms have the indicated meanings:

| | |
|---|---|
| 7-ACA | 7-Aminocephalosporanic acid |
| 7-ADAC | 7-Aminodeacetylcephalosporanic acid |
| 7-ADCA | 7-Aminodesacetoxycephalosporanic acid |
| 6-APA | 6-Aminopenicillanic acid |
| DAOC | Desacetoxycephalosporanic acid |
| DAOCS | DAOC synthetase |
| DAC | Deacetylcephalosporin C |
| DACS | DAC synthase |
| IPNS | Isopenicillin N synthetase |
| Tris | Tris[hydroxymethyl]aminomethane |
| EDTA | Ethylenediaminetetraacetic acid |
| DEPC | Diethylpyrocarbonate |
| TE | Tris/EDTA buffer |
| SSC | Salt (Sodium chloride), sodium citrate buffer |
| SDS | Sodium dodecylsulfate |
| PEG | Polyethylene glycol |

*Penicillium chrysogenum* Culture

The first step of the method of the present invention comprises the step of maintaining in a culture medium capable of sustaining its growth, a strain of *Penicillium chrysogenum* which produces isopenicillin N and adding to said culture medium an adipate feedstock comprising any one or more of adipic acid, or its salts and esters which are capable of being assimilated and utilized by said strain of *Penicillium chrysogenum* to produce adipoyl-6-APA. The adipate feedstock may be added to the culture medium after inoculation with *P. chrysogenum,* but it is preferred that it already be present in the culture medium at the time that inoculation takes place.

Other genera than Penicillium, e.g., *Aspergillus nidulans,* as well as other species of the genus Penicillium besides the *chrysogenum* species produce isopenicillin N. However, historically the highest producing strains of isopenicillin N have all been developed by well-known techniques of strain improvement from the *chrysogenum* species. As a practical matter, then, the present invention has been limited to strains of *Penicillium chrysogenum,* although its applicability to other species is obvious. Any deposited strain of *Penicillium chrysogenum* or other publicly available source of such strain is a suitable starting point for carrying out the method of the present invention.

The culture medium capable of sustaining the growth of a strain of *Penicillium chrysogenum* which produces isopenicillin N is of the type with which the person of ordinary skill in the art would be readily familiar. For example, the culturing would be carried out by the submerged aerobic fermentation method, and the medium employed would be selected from a number of suitable media available. Typical media utilize carbon sources such as sucrose, glucose, and starch; nitrogen sources such as soybean meal and grits, cotton seed oil, peanut meal, and various amino acids, mixtures thereof, and peptones. Production requirements emphasize yield and ease of isolation, and thus preferred media for such situations may be molasses as the carbon source and soybean meal and amino acids as the nitrogen source.

Nutrient inorganic salts are commonly added to the culture medium, and include salts capable of supplying the following ionic components: sodium, potassium, ammonium, calcium, phosphate, sulfate, chloride, bromide, nitrate, carbonate, ferric, ferrous, magnesium, manganese, etc. Trace elements are also usually essential for the growth, development and metabolism of the *Penicillium chrysogenum*, and can be added directly to the culture medium unless supplied already as contaminants, essentially, of the other culture medium ingredients.

The *Penicillium chrysogenum* strains can be cultured in equipment of small volume such as 1 L shake flasks where it is desired to produce only small quantities of adipoyl-7-ACA, and eventually 7-ACA. Where larger quantities of the adipoyl-7-ACA are desired, however, large scale fermentation tanks under submerged aerobic fermentation conditions will be employed.

In carrying out the large scale preparation of adipoyl-7-ACA, spores of the *Penicillium chrysogenum* strain are maintained on an agar slant. The spores from the slant are employed to inoculate a vegetative medium having a small volume. The vegetative medium is incubated to produce a heavy, fresh, actively growing culture of the microorganism. This vegetative growth is then employed as the inoculum for the large scale fermentation medium. In certain instances it may be desirable to include yet a further vegetative medium as the inoculum for the fermentation medium. Such second stage vegetative media are commonly employed when the volume of the fermentation medium is significantly larger than the first vegetative medium. In this manner, the spores of the microorganism are cultured at: first in a small volume of vegetative medium to obtain inoculum for a vegetative medium of larger volume. The larger volume vegetative medium then supplies sufficient concentration of the microorganism to initiate a rapid onset of the fermentation in the large scale fermentation tank. The vegetative medium can have the same composition as the fermentation medium or it can contain additional ingredients to spur the growth and development of the microorganism on a small scale.

The *Penicillium chrysogenum* strains employed in the method of the present invention are most effectively cultured at temperatures between about 20° and 30° C., but optimal yields will be obtained when the temperature is between about 22° and 28° C., preferably about 25° C.

Maximum production of adipoyl-7-ACA occurs when the *Penicillium chrysogenum* strain is cultured in large scale tanks for a period of between about 10 and 30 days, preferably 15 to 25 days. However, when cultured in small scale apparatus, such as 250 mL shake flasks, the growth of the microorganism is more rapid and it produces adipoyl-7-ACA in a shorter time, e.g., 4 to 15 days, frequently 5 to 7 days.

If the terminal pH in large scale fermentation tanks reaches 8.0 or higher, yield of adipoyl-7-ACA may be adversely affected. In such situations, it is desirable to monitor the pH of the culture medium throughout the fermentation. If it appears that the pH will reach such levels prior to the time of maximum production of adipoyl-7-ACA occurs, the pH can be conveniently adjusted downward by adding a suitable acid or buffering agent to the fermentation medium.

The production of adipoyl-7-ACA can be followed by testing samples of the fermentation broth chromatographically.

As with most submerged aerobic fermentations, sterile air is passed through the culture medium to obtain more efficient growth of the *Penicillium chrysogenum* strain and increased production of adipoyl-7-ACA. The volume of air forced through the culture medium is usually at least approximately 0.2 volumes of air per minute per volume of culture medium. However, an increased rate of air passage can often have a beneficial effect on the production of adipoyl-7-ACA.

The *Penicillium chrysogenum* strain will typically produce, in addition to adipoyl-7-ACA, many side products and metabolites. Since some of these are acid labile, it is desirable in the recovery of adipoyl-7-ACA from the fermentation medium, to treat the whole fermentation broth at an acid pH for a short time in order to destroy some of the co-produced impurities. The adipoyl-7-ACA fermentation product is recovered from the filtered fermentation broth thus treated and optionally may be separated from the other components of the fermentation medium by chromatography over an ion exchange resin and may be further purified by chromatography if necessary before the subsequent step of enzymatic cleavage of the adipoyl side chain. It is also possible to carry out such ion exchange chromatography separation after side chain cleavage has been carried out. One of the major side products which presents separation problems is adipoyl-6-APA, and it is possible to chemically or enzymatically degrade this side product in order to make separation more facile. Initially, the filtered fermentation broth is subjected to al preliminary purification procedure which can include an initial extraction with a water immiscible organic solvent, such as n-butanol or amyl acetate, to remove impurities. The extracted broth can then be further purified in a preliminary manner by chromatography over activated carbon.

Addition of Adipate Feedstock

Preferably, at the time the fermentation culture for the *Penicillium chrysogenum* is established as described above, i.e., prior to inoculation, an adipate feedstock is added to the other ingredients of the fermentation culture medium. Optionally, the adipate feedstock may be added at some time after inoculation, e.g., at 1, 2 and/or 3 days after inoculation. The adipate feedstock is defined as any one or more of adipic acid, or salts or esters of adipic acid which are capable of being assimilated and utilized by the strain of *Penicillium chrysogenum* being cultured to produce adipoyl-6-APA. The adipic acid, salts and esters may be used alone or in any combination. The disodium salt is preferred, although potassium and mixed salts with sodium would also be suitable. The methyl ester could be used, but the ethyl ester is water insoluble. The adipic acid salt or ester must be such that it can be assimilated and utilized by the strain of *Penicillium chrysogenum* to make adipoyl-6-APA. For example, adipic acid itself might be suitable, even though it is water insoluble, if under proper pH conditions an assimilatable salt is formed.

Suitable Expandase and/or Hydroxylase Enzymes

The strain of *Penicillium chrysogenum* which has been cultured and provided with an adipate feedstock as described above so that it produces adipoyl-6-APA, is also one which has been transformed by DNA encoding the activity of the expandase and hydroxylase enzymes, whereupon as a result of its expression, said adipoyl-6-APA is in situ ring-expanded to form adipoyl-7-ADCA, and the 3-methyl side chain is also converted to 3-hydroxymethyl.

The adipoyl-6-APA is produced intracellularly by the adipate feedstock cultured *Penicillium chrysogenum*. In that intracellular setting, i.e., on an in situ basis, the transformed *Penicillium chrysogenum* also expresses DNA encoding the activity of the expandase and hydroxylase enzymes, whereupon the enzymes operate on the adipoyl-6-APA as a substrate, and ring-expand it to form adipoyl-7-ADCA, which is then hydroxylated to adipoyl-7-ADAC (adipoyl-7-aminodeacetylcephalosporanic acid).

The novel bioprocess of the present invention includes within its scope the transformation of a *Penicillium chrysogenum* strain of the type described above with any DNA encoding the activity of the expandase and hydroxylase enzymes, whereupon as a result of their expression, adipoyl-6-APA is in situ ring-expanded to form adipoyl-7-ADCA, and then hydroxylated to form adipoyl-7-ADAC. Thus, the DNA with which the *Penicillium chrysogenum* is transformed must express enzymes having not only the activity of the expandase enzyme as understood in the art, i.e., the ability to ring-expand isopenicillin N to DAOC, but the ability to ring-expand adipoyl-6-APA to adipoyl-7-ADCA. In addition, the hydroxylase enzyme must be capable of hydroxylating the adipoyl-7-ADCA to adipoyl-7-ADAC.

Two alternative approaches are considered to be suitable embodiments within the scope of the present invention with respect to the manner in which the expandase and hydroxylase enzyme activities are provided. In one embodiment, which is preferred, the expandase and hydroxylase functions are accomplished by the activity expressed by a single, although essentially bifunctional, gene of *Cephalosporium acremonium*, with which the *P. chrysogenum* is transformed. This gene, which expresses both the expandase and hydroxylase activities together, will be referred to as the expandase/hydroxylase gene, as will its gene product, the expandase/hydroxylase enzyme(s). Typically, when *P. chrysogenum* is transformed with the DNA from *C. acremonium* encoding the expandase/hydroxylase activity, the expression of this activity will be controlled by a single promoter sequence, indicating the presence of a single gene An alternative embodiment of the present invention, which is equally suitable, involves transforming the *P. chrysogenum* host with DNA encoding the expandase and hydroxylase activities as separate genes, as opposed to a single expandase/hydroxylase gene. It should be noted that separate expandase and hydroxylase genes and the corresponding enzymatic activities which they encode are found in prokaryotic microoganisms such as *S. clavuligerus*, rather than in eukaryotic microoganisms such as *C. acremonium*, which encode the single expandase/hydroxylase gene and enzyme, as already observed above.

The sequence of the prokaryotic hydroxylase enzyme and nucleotides encoding it are described in Kovacevic, et al., *J. Bacteriol.*, 173(1), 398–400 (1991) and EP-A-0 465 189, as is the means for isolating said enzyme. As the skilled artisan will appreciate, from the sequence of the hydroxylase, it is possible to synthesize by well-known manual methods or automated DNA synthesizers, the DNA encoding the hydroxylase enzyme. The DNA compound or alternate sequences encoding the same amino acid sequence of the hydroxylase, or fragments or derivatives thereof having equivalent hydroxylase activity, in turn, may be used as the basis for preparing various cloning and expression vectors when combined with promoter and other regulatory sequences, with which it is then possible to transform the *P. chrysogenum* host in order to express the hydroxylase enzyme and thereby carry out the method of the present invention. It is also possible to use the DNA compound as a probe with which to screen the genomic library of a candidate strain potentially containing a useful hydroxylase enzyme, in order to identify homologous sequences by hybridization. The activity of any putative hydroxylase thus identified can be confirmed by using the actual adipoyl-7-ADCA substrate of the method of the present invention and isolating its hydroxylation product by HPLC.

When this embodiment of the present invention is used, i.e., a single gene expressing only hydroxylase activity, it will then be necessary to also separately provide for DNA encoding the activity of the expandase enzyme, so that the *P. chrysogenum* can be transformed by a suitable expression vector which allows in situ expression of the expandase function to provide the ring expansion step in the method of the present invention. Many expandase enzymes are known; and, it is contemplated, based on side chain similarity, that many expandase enzymes will be operable in the novel bioprocess of the present invention.

Other useful embodiments of the present invention are based on the fact that DNA encoding the activity of more than one expandase and/or more than one hydroxylase may be used to transform the non-recombinant *P. chrysogenum* strain. It is possible with such embodiments to obtain enhanced expandase and/or hydroxylase activity because of the increased amounts of enzymatic protein which are expressed.

It has already been noted under the section describing the prior art, that the expandase enzyme derived from *Streptomyces clavuligerus* ATCC 27064 has been fully sequenced as well as characterized by endonuclease restriction mapping. However, what would appear to be the same enzyme, derived from *S. clavuligerus* NRRL 3585, has been reported to have a different molecular weight, but it has not been sequenced. And, as also described above in the section dealing with the prior art, the DAOCS/DACS enzyme from *Cephalosporium acremonium* ATCC 11550 has been sequenced [Samson et al., *Bio/Technology* (1987) 5: 1207–1214, and EP-A-0 281 391].

These expandase enzymes already identified in the prior art are useful in the novel bioprocess of the present invention. Other expandase enzymes not yet identified, derived from different strains of *S. clavuligerus* or *C. acremonium*, or even from microorganisms of different genera, may also prove to be suitable for carrying out the novel bioprocess of the present invention. The procedures for identifying such new strains and genera of useful microorganisms and for isolating the putative expandase enzymes and establishing that they are suitable for use in the method of the present invention, are straightforward and well within the skill of the artisan. Screening of cell-free extracts of candidate new strains and genera of useful microorganisms may be done in a reliable and reproducible manner by adding said extracts to the adipoyl-6-APA substrate in the presence of known DAOCS co-factors which include ferrous ($Fe^{2+}$) ions, ascorbate, α-ketoglutarate and adenosine triphosphate (ATP). Adipoyl-6-APA may be prepared in sufficient quantities by feeding an adipate feedstock to an untransformed *Penicillium chrysogenum* in a manner analogous to that describer in detail further below. The desired expandase (or expandase/hydroxylase) enzyme is present if adipoyl-7-ADCA and/or adipoyl-7-ADAC is formed, the presence of which may be detected by chromatography.

It is also possible, using well-known recombinant techniques, to generate DNA probes, based on the nucleotide sequences of the expandase genes from *S. clavuligerus* and *C. acremonium,* for example, to screen the DNA contents of a candidate microorganism likely to produce an expandase suitable for use in the method of the present invention.

Potential Sources for Expandase, Hydroxylase and Expandase/Hydroxylase Enzymes

Expandase enzymes, as already noted, are enzymes which catalyze the expansion of penam ring structures (found in penicillin-type molecules) to ceph-3-em rings (as found in the cephalosporins). Any organism producing metabolites which contain a cephem ring is, therefore, a potential source for an expandase-encoding DNA. Likewise, any organism which produces cephalosporins containing a 3-hydroxymethylgroup is a potential source of hydroxylase- (or expandase/hydroxylase-) encoding DNA. Examples of such organisms are listed below, but this list is exemplary only and should not be considered exhaustive:

FUNGI

*Cephalosporium acremonium*
Cephalosporium sp.
Emericellopsis
Paecilomyces
Scopulariopsis
Diheterospora
Spiroidium
Anoxiopsis

ACTINOMYCETES

*Streptomyces clavuligerus*
*S. lipmanii*
*S. wadayamensis*
*S. todorominensis*
*S. filipinensis cephamycini*
*S. heteromorphus*
*S. panayensis*
*S. griseus*
*S. cattleya*
*Nocardia lactamdurans*

OTHER BACTERIA

Flavobacterium sp.
*Alcaligenes denitrificans*
*Mycoplana bullata*
*Providencia rettgeri*
*Lysobacter lactamgenus*

The expandases and hydroxylases of the organisms listed above are merely candidates for further investigation, and it may be that not all of them will be suitable for the novel process of the present invention.

Isolating DNA Fragments Encoding Expandase Activity

Once the presence of a desired expandase enzyme has been detected in the manner described above, procedures for the isolation of the DNA encoding the expandase enzyme activity are also straightforward and well known in the art. DNA probes based on the known sequences and partial sequences of the genes encoding the expandase enzymes are constructed which will hybridize to the desired enzyme-encoding DNA to be isolated. The construction of such probes is based on a knowledge of the amino acid and nucleotide base-sequence encoding the expandase enzyme, as well as the codon preferences of the particular microorganism involved. A detailed description of typical procedures of this type applied to the genomic DNA of *Streptomyces clavuligerus* ATCC 27064 is set out further below.

Isolation of the DNA encoding the expandase enzyme activity is accomplished using the restriction and ligation procedures well known in recombinant DNA technology. It is necessary to have an endonuclease restriction map of the genome of the microorganism involved, so that the proper restriction fragment can be produced and isolated. Restriction maps for *S. clavuligerus* and *C. acremonium* are already available; thus, for the former, restriction enzymes Bam HI and Sal I are used and electrophoresis provides the desired 1.8 to 2.2 kb sized fragments.

Sources of Acetyltransferase Enzyme and Isolating DNA Fragments Encoding Said Activity Cloning of the *C. acremonium* DAC acetyltransferase gene may be carried out in accordance with recombinant techniques well known in the art, which are described in general terms immediately below.

In order to clone the acetyltransferase gene, mutants of *C. acremonium,* deficient in the ability to convert deacetyl-cephalosporanic acid (DAC) to cephalosporin C must first be generated. Such a process entails subjecting *C. acremonium* cells to mutagens such as N-nitrosoguanidine (NTG), nitrous acid or ultra-violet light, allowing recovery on a suitable growth medium and then assaying by, e.g., chromatographic or biological means, for the accumulation of DAC.

On the identification of a suitable mutant the ext step in identifying the gene encoding theacetyltransferase is the isolation of *C. acremonium* DNA from a cephalosporin C producing strain. Following cleavage, either by restriction endonuclease digestion or mechanical shearing, into suitable-sized fragments, it is incorporated into plasmid, or cosmid, transformation vectors also containing a suitable dominant marker gene such as that for hygromycin or phleomycin resistance. The vector should also contain DNA sequences to facilitate the subsequent recovery of the inserted DNA, e.g., lambda (phage) cos sites which allow rescue of cloned DNA by in vitro packaging followed by infection of *E. coli,* which can be carried out by well established procedures.

Protoplasts of the acetyltransferase-minus mutant strain are then transformed using the vectors containing random fragments of genomic DNA and transformants selected on the basis of antibiotic resistance. Transformants can then be assayed for the restoration of cephalosporin C production, this being an indication of successful complementation by a vector-contained acetyltransferase gene. Mutants suspected of harboring cloned copies of the gene can then be grown up, their DNA isolated and the vector DNA recovered by the method outlined above. Confirmation that the vector indeed contains the acetyltransferase gene is obtained by subcloning into *E. coli,* using standard procedures and readily available vectors, followed by re-transformation of the acetyltransferase-minus mutant. The gene can then be isolated, sequenced and manipulated as described in the working examples herein using techniques employed routinely by these of ordinary skill in the art of molecular genetics.

Following alternative procedures also well known in the art, Matsuda et al. isolated and sequenced the gene encoding the acetyltransferase activity of *C. acremonium,* as well as the deduced amino acid sequence of the enzyme itself, as disclosed in EF-A-0 450 758. These alternative procedures consisted of isolation of the acetyltransferase enzyme, N-terminal amino acid sequencing, and from this information deducing the nucleotide sequence encoding this portion of the enzyme. From this information in turn, probes are generated which hybridize to the full encoding sequence, permitting its isolation.

Transformation of the *Penicillium chrysogenum* Strain

Once the DNA fragments encoding the expandase/hydroxylase, expandase and hydroxylase, and acetyltransferase activities are obtained, they may be inserted (ligated) into a plasmid or other expression vector, along with DNA fragments comprising promoters, translational activating sequences, resistance markers, regulatory sequences, cosmid formers, and any other DNA sequences which permit or promote transformation, drive expression of the gene products, and facilitate isolation of the transformants. The expression rector which has thus been constructed is then used to achieve transformation of the *Penicillins chrysogenum* strain and intracellular expression of the activity of the expandase/hydroxylase, expandase and hydroxylase, and acetyltransferase enzymes. The techniques used to achieve transformation and expression are well known in the art, and a detailed description of such typical procedures is set out further below.

As already detailed further above, the transformed *Penicillium chrysogenum* strain expresses the activity of the expandase/hydroxylase, expandase and hydroxylase, and acetyltransferase enzymes intracellularly, which then respectively operate in situ on the adipoyl-6-APA substrate to ring-expand it to adipoyl-7-ADCA, hydroxylate the latter to adipoyl-7-ADAC, which is then acetylated to adipoyl-7-ACA.

Novel Transformant

The specific *Penicillium chrysogenum* transformants expressing the activities encoded by the expandase/hydroxylase and expandase/hydroxylase plus acetyltransferase genes which are the preferred embodiments of the present invention, are novel with respect to similar constructions in the prior art, such as those in Cantwell et al. (1990) *Current Genetics*, 17, 213–221, EP-A-0 281 391, and EP-A-0 437 378. The Cantwell construction has the *Streptomyces clavuligerus* expandase gene placed under the control of the *P. chrysogenum* isopenicillin N synthetase (IPNS) promotor and so differs from the constructs of the present case in the lack of any DNA encoding hydroxylase or acetyltransferase activities.

Ingolia et al. in EP-A-0 281 391 describe *P. chrysogenum* transformation vectors which contain DNA encoding the *C. acremonium* expandase/hydroxylase bifunctional enzyme with expression driven by the Penicillium IPNS promotor. In fine of these constructions (pPS62), the expandase/hydroxylase gene is fused downstream of and in frame with the hygromycin phosphotransferase gene. The gene product, a hygromycin phosphotransferase::expandase/hydroxylase fusion protein, differs from the product of the present invention, an expandase/hydroxylase enzyme essentially identical to that produced in *C. acremonium*. The other vector described in EP-A-0 281 391 was constructed through an extensive series of molecular manipulations, including the use of synthetic DNA linkers. The final construction (pPS61) utilizes the 1.2 kb NcoI fragment of the Penicillium IPNS promoter to express the expandase/hydroxylase gene, and the *Aspergillus nidulans* acetamidase gene as a selectable marker for transformation of Penicillium. The sequence of codons nine and ten in the expandase/hydroxylase gene, encoding arginine and leucine, respectively, are changed from CGTCTC to CGCCTA, which does not change the encoded amino acid sequence.

In the construction of the present invention, the 1.2 kb NcoI IPNS promoter fragment was fused to the expandase/hydroxylase gene without altering the native expandase/hydroxylase gene sequence. The IPNS promoter used for the construction of the present invention has two separate four base duplications relative to the native promoter, one at the SalI site 760 bp upstream of the ATG start codon and the other at the XbaI site five base pairs upstream of the start codon and within the 5' untranslated leader sequence. Tnese chantges do no affect high level expression of the expandase/hydroxylase gene.

A further difference in the vectors lies in the selectable markers used. Those constructs described in EP-A-0 281 391 use acetamidase and hygromycin as selectable markers. This is in contrast to the expandase/hydroxylase Penicillium transformation vector utilized in the present invention (pPEN/CEPH-1) which contains the phleomycin resistance marker. A *Penicillium chrysogenum* strain transformed with the vector pPEN/CEPH-1 and capable of expressing expandase/hydroxylase activity has been identified as PC200. Its taxonomic features typically include the production of broadly spreading colonies, blue-green to green in color, smooth velvety with yellow drops; reverse yellow diffusing into the agar; conidial heads branched with all parts smooth; conidia elliptical to globase 3–4 $\mu$m in length. Acceptable culture conditions for the *P. chrysogenum* utilize a solid medium comprising lactose, monohydrated 1.5% (w/v); corn steep liquor, 0.5% (v/v); peptone, 0.5% (w/v); NaCl, 0.4% (w/v); $MgSO_4$—$7H_2O$, 0.05% (w/v); $KH_2PO_4$, 0.06% (w/v); $FeCl_3$—$6H_2O$, 0.0005% (w/v); $CuSO_4$—$5H_2O$, 0.0002% (w/v); agar, 3.0% (w/v); in one liter of distilled water, pH 4.8. The *P. chrysogenum* just described and designated PC200, has been deposited with the American Type Culture Collection (ATCC), 12301 Parklawn Drive, Rockville, Md. 20852, under the accession number ATCC 74186 (date of deposit: Sep. 23, 1992).

The second novel *Penicillium chrysogenum* transformant of the present invention capable of producing adipoyl-7-ACA expresses both expandase/hydroxylase and acetyltransferase activities by virtue of having been transformed with a single vector (pTS-8) comprising DNA encoding both of these enzymes. This vector, therefore, differs from those Penicillium transformation vectors mentioned in EP-A-0 437 378 which comprise DNA encoding either the *C. acremonium* acetyltransferase alone or in connection with a DNA sequence coding for a mutant expandase/hydroxylase polypeptide. In the pTS-8 construction, expression of the expandase/hydroxylase and acetyltransferase genes are each driven by separate copies of the *P. chrysogenum* IPNS promotor; a third copy of the IPNS promoter is used to drive transcription of the phleomycin resistance gene used as the selectable marker.

In an alternative embodiment of the present invention, the expandase/hydroxylase and acetyltransferase genes can be incorporated in separate vectors and introduced into the host Penicillium strain in sequential fashion. The order in which the DNA fragments encoding the expandase/hydroxylase and acetyltransferase enzyme activities are introduced into the Penicillium strain is important only from a practical stand-point. Preferably, the transformation of the Penicillium with the expandase/hydroxylase gene(s) should precede the insertion of the acetyltransferase gene since this is the order in which the enzymes work in vivo. Therefore, the expression of the expandase/hydroxylase can be monitored by assaying for adipoyl-7-ADAC production. Adipoyl-7-ADAC being the substrate for the acetyltransferase enzyme, expression of the subsequently introduced acetyltransferase-encoding gene is indicated by the production of adipoyl-7-ACA. Using a suitable in vitro assay for the acetyltransferase, it is possible to transform the Penicillium with the acetyltransferase gene first, confirm its expression using the in vitro assay, and then go on to introduce the expandase/hydroxylase gene. Either route would, therefore, be a suitable embodiment of the process of the present invention for making 7-ACA.

The preferred embodiment, however, has all three enzyme activities introduced simultaneously through the construction of a single plasmid vector comprising the DNA encoding the expandase/hydroxylase and acetyltransferase activities of *C. acremonium*. A *Penicillium chrysogenum* strain transformed with such a single plasmid vector, the vector pTS-8, and capable of expressing expandase/hydroxylase and acetyltransferase activity has been identified as PC300. Its taxonomic features are the same as those described further above for PC200. Acceptable culture conditions for PC300 are the same as those described further above for PC200. The *P. chrysogenum* strain designated PC300 has been deposited with the American Type Culture Collection (ATCC), 12301 Parklawn Drive, Rockville, Md. 20852, under the accession number ATCC 74187 (date of deposit: Sep. 23, 1992).

The specific *Penicillium chrysogenum* transformed with the vector pPenFTSO expressing the activity of the *S. clavuligerus* expandase gene which is a preferred embodiment of the present invention is novel with respect to such constructions in the prior art as that in Cantwell et al. (1990) *Current Genetic*, 17, 213–221. In both constructions, a vitro mutagenesis is used to connect the promotor to the expandase gene. In the Cantwell construction, manipulation introduces a NdeI site at the ATG of the expandase gene which is ligated to the XbaI site at the 3' end of the IPNS promotor by a XbaI/NdeI linker. In the construction of the present invention, an NcoI site is created at the ATG of the expandase gene and ligated to the NcoI site at the 3' end of the IPNS linker. This creates the following sequences around the promotor-gene junctions in these constructions:

|  | XbaI NcoI |  |
|---|---|---|
| IPNS promotor | 5' TCTAGACACCATGG 3' | SEQ ID NO:1 |
| Strep expandase | 5' GTGAGAGTTGATGGAC 3' | SEQ ID NO:2 |
| Gantwell | 5' TCTAGACAC<u>T</u>ATGGAC 3' | SEQ ID NO:3 |
| Present Invention | 5' TCTAGACAC<u>C</u>ATGGAC 3' | SEQ ID NO:4 |

The Cantwell construction replaces a C with a T, whereas, in the construct of the present invention the C is retained; thus the sequence of the IPNS promotor immediately adjacent to the ATG start codon exactly matches that which is found with the naturally occurring IPNS gene. It is possible that the promoter of the prior art, although differing by only a single nucleotide base, may lead to a lower efficiency of translation efficiency, and consequently to a lower level of expandase gene expression.

Other differences are in the regions of the promotor or gene included in the constructions. The Cantwell construction contains the 5' BamHI to XbaI 3' region of the IPNS promotor, whereas, the vector of the present invention contains the 5' NcoI to NcoI 3' region of the promotor [Diez, et al., (1990), *J. Biol. Chem.* 265, 16358–163653]. This results in approximately 250 bps additional on the 5' end of the IPNS promotor in the Cantwell construction. However, this region is in the open reading frame of the ACV synthetase gene upstream of the IPNS gene.

The Cantwell construction also contains the Streptomyces gene from the ATG to the BamHI site 3' of the gene, whereas the vector of the present invention contains the ATG to the SalI site 3' of the gene [Kovacevic et al. (1989), *J. Bacteriol.*, 171, 754–7603]. This results in approximately 1000 bps of additional 3' end sequence on the Cantwell construction. The construction of the present invention still contains the upstream region of the expandase gene to the BamHI site 5' of the ATG; however, it is separated from the reading frame of the expandase gene by the IPNS promotor.

Another difference of the pPenFTSO construct of the present invention over that described in the prior art relates to the selectable marker which is used. The use of a Penicillium IPNS promoter: phleomycin gene fusion in the construct of the present invention tends to select for integration of multiple copies or integration at loci that allow high level expression, and thus potentially may give a higher percentage of transformants that express the expandase gene at high level.

Cleavage of the Adipoyl Side Chain

The last step in the novel bioprocess of the present invention is the cleavage of the adipoyl side chain from the adipoyl-7-ADAC or adipoyl-7-ACA, which requires treatment of the products of the preceding steps with an adipoyl amidase enzyme. As already noted above, one of the significant achievements of the present invention is the ability to carry out all of the steps leading up to formation of the adipoyl-7-ADAC and adipoyl-7-ACA in a single fermentation culture. This achievement provides exceptionally improved efficiency in not having to isolate and partially purify intermediate products from step to step of the process. In this last step, however, the adipoyl amidase enzyme system is not present, i.e., has not been generated in situ in the original fermentation culture, either by natural or recombinant expression of the genes of *P. chrysogenum*.

If the novel bioprocess of the present invention is being carried out in a batch-wise manner, then it will be necessary to isolate and partially purify the product of the first step, and preliminary procedures for doing this have already been described above.

Nevertheless, the process of the present invention may be carried out in any way which effectively brings the adipoyl amidase into contact with the adipoyl-7-ADAC or adipoyl-7-ACA so that enzymatic conversion of that compound to 7-ADAC or 7-ACA can take place. This is the definition of the term "contacting" in its broadest context. It is possible to employ a cell free broth of crude adipoyl-7-ADAC or adipoyl-7-ACA as the feed stream and treat it in a batch-wise fashion with crude adipoyl amidase broth. This approach realizes some efficiencies since it does not require any substantial purification of the reactants initially. Of course, modifications are possible. E.g., the reactants may be purified to whatever extent desired before being brought into contact with each other. Also, it would be possible to carry out the process in a continuous manner rather than batch-wise. The contacting of the reactants themselves may be modified in various ways in keeping with advances in process technology. Thus, an immobilized enzyme may be used, e.g., in the form of a column containing the adipoyl acylase with the adipoyl-7-ADAC or adipoyl-7-ACA being passed through the column. The immobilized enzyme may also be added to the adipoyl-7-ADAC or adipoyl-7-ACA solution as a suspension. Such immobilized enzyme systems offer the advantages of easy enzyme recovery and multipler use. Another example of such process technology is that relating to membrane reactors. The preferred method of contacting the reactants is by way of the immobilized enzyme column.

Adipoyl Amidase Enzymes Useful in the Cleavage Step

There are a number of enzymes with known specificity towards adipoyl side chains. Results obtained with an adipoyl amidase commercially available from the RAEV Corp. are detailed in the working examples further below. Seven other enzymes have been reported in the literature which remove adipoyl side chains from cephalosporin-type molecules. Six of these seven enzymes are from Pseudomonas species, and the seventh is from a Bacillus species. Some similarities exist between certain of the Pseudomonad enzymes, but all seven differ to some extent in their physical/biological properties. Some of their characteristics are summarized below:

| ENZYME (Pseudomonas and Bacillus strains) | REFERENCE | APPROX. MOL. WT. (Subunit) |
|---|---|---|
| P. SY-77-1 (Toyo Jozo) | Shibuya, et. al. (1981) | Apparently same as GK 16 below |
| P. GK16 (Asahi) | Matsuda, Komatsu (1985) | 16,000 54,000 |
| P. SE83 (acyI) (Asahi) | Matsuda, et al. (1987) | 38,200 19,900 |
| P. SE83 (acyII) (Asahi) | Matsuda, et al. (1987) | 25,400 58,200 |
| P. diminuta N176 (Fujisawa) | Aramori, et al. (1991a)* | 58,000 26,000 |
| P. diminuta V22 (Fujisawa) | Aramori, et al. (1991a)* | ? ? |

-continued

| ENZYME (Pseudomonas and Bacillus strains) | REFERENCE | APPROX. MOL. WT. (Subunit) |
|---|---|---|
| Bacillus laterosporus J1 (Fuji.) | Aramori, et al. (1991b)** | 70,000 (monomeric) |
| Pseudomonas sp. (RAEV Corp.) | — | 16,000 54,000 |

*Aramori et al., J. Ferment. Bioeng. (1991) 72: 232–243.
**Aramori et al., J. Bacteriol. (1991) 173: 7848–7855.

All of the above adipoyl amidase enzymes are useful in the novel bioprocess of the present invention. Other adipoyl amidases useful in the method of the present invention may be readily discovered by testing the candidate enzyme against adipoyl-7-ACA and adipoyl-7-ADAC, the actual substrates upon which it must operate. A positive result gives a reliable and reproducible method of determining that a candidate enzyme is indeed useful in the method of the present invention. The substrate can be prepared from the reaction of adipic anhydride with 7-ACA using a modification of the procedure reported by Szewczuk and Wellman-Bednawska in Clin. Chim Aeta (1978) 84, 19–26. It is also possible to adapt the method described in Agric. Biol. Chem. (1981) 45(7), 1561–1567, which is one for preparing glutaryl-7-ACA. The adipic anhydride may be prepared in accordance with the method of Albertson and Lundmark described in J. Macromol. Sci. Chem. (1990) A27, 397–412. The 7-ACA is available from several commercial sources, including Sigma Chemical Co.

If it is desired to carry out a rough screening of candidate enzymes using a rapid colorimetric method, one may substitute for the adipoyl-7-ACA substrate a calorimetric substrate such as adipoyl-PABA (para-aminobenzoic acid) or adipoyl-pNA (para-nitroaniline). Such a method may be adapted from that described for γ-glutamyl PABA in Szewczuk et al., Clinica Chimica Acta, 84 (1978) 19–26. Cleavage of the side chain gives a color generating species whose presence and concentration is readily determined using a colorimeter. For more detailed information concerning these and other suitable calorimetric methods, see Marelli, L. P. (1968) J. Pharm. Sci. 57: 2172–2173; Szasz, G. (1969) Clin. Chem. 15: 124–136; Szewczuk, A. et al. (1980) Anal. Biochem. 103: 166–169; and Reyes, F. et al. (1989) J. Pharma. Pharmacol. 41: 136–137.

A comparison was made of the N-terminal amino-acid sequences of the RAEV enzyme with the large subunits of acyII and the GK16 enzymes set out in the table above. The results of the comparison are shown below (where parentheses indicate less than conclusive assignments):

```
RAEV  - SEQ ID NO:5
  (S) N (S) (G) A V A P G K T A N G N A L (L) L Q N (P)
GK16  - SEQ ID NO:6
   S  N  S   W  A V A P G K T A N G N A L  L  L Q N  P
acyII - SEQ ID NO:7
   S  N  N   W  A V A P G R T A T G R P I  L  A G D  P
```

From the sequences shown, it is apparent that all three of these peptides are related. However, a protein having an N-terminal sequence similar to those shown above will not necessarily possess adipoyl amidase activity, as is the case with a penicillin G acylase produced by a strain of Arthrobacter. On the other hand, there are adipoyl amidases useful in the method of the present invention which do not exhibit significant homology to the above N-terminal sequence. For example, the Asahi acyI and Fujisawa B. laterosporus J1 acylases set out in the table further above, which have been shown to have some adipoyl-7-ACA acylase activity, do not share any sequence homology with the other enzymes set out above. Consequently, the scope of the present invention with respect to the adipoyl amidases useful in the last step of the novel bioprocess is determined by whether or not a candidate enzyme is able to cleave the adipoyl side chain from adipoyl-7-ACA, a matter which may be determined readily and reliably, as detailed above.

DESCRIPTION OF PREFERRED EBODIMENTS

There follows a detailed description of certain preferred embodiments of the present invention, but these are intended to be illustrative only, and not in any way a limitation of the present invention.

EXAMPLE 1

Penicillium chrysogenum Culture Conditions

The Penicillium chrysogenum strains used in these procedures were maintained on plate containing LCSB medium composed of lactose, monohydrated, 1.5%(w/v); corn steep liquor, 0.5%.(v/v); peptone, 0.5%(w/v); NaCl, 0.4%(w/v); $MgSO_4$—$7H_2O$, 0.05%(w/v); $KH_2PO_4$, 0.06% (w/v);

FeCl$_3$—6H$_2$O, 0.0305% (w/v); CuSO$_4$—5H$_2$O, 0.0002% (w/v); agar, 3.0% (w/v); in one liter of distilled water, pH 4.8. After 12 days at 25° C. and 65% relative humidity, single colonies were removed and added to 2 mL of sterilized water in a screw-top tube containing glass beads. After macerating the culture growth by vortexing, the suspension was used to inoculate rice flasks. The rice flasks contained 25 g/250 mL flask of Uncle Ben's converted rice, natural long grain, which has been washed with three to four volumes of distilled water for seven minutes, mixed every 30 seconds, and then drained until the water uptake into the rice was approximately 25%. After 12 days at 25° C. and 65% humidity, the spores were washed from the rice with 50 mL of sterile water. The spore suspension was used to inoculate liquid cultures and also to provide lyophiles of the cultures for storage at 4° C. The spores were added to an equal volume of 5% skim milk and lyophilized in sterile ampoules.

A two-stage fermentation of the strain in shake-flasks was used for the production of penicillins or for the production of mycelia as a source of RNA or DNA. The seed stage was initiated by adding 1×10$^8$ spores to 50 mL/500 mL flask of medium composed of glucose, 3.0% (w/v); pharmamedia, 1.0% (w/v); corn steep liquor, 3.0% (v/v); ammonium sulfate, 0.2% (w/v), CaCO$_3$, 0.5% (w/v); monopotassium phosphate anhydrous, 0.05% (w/v); lactose, 1.0% (w/v); primary dry yeast, 1.0% (w/v) in one liter of distilled water. Incubation was a—25° C. and 65% relative humidity on a rotary shaker with a 70 mm diameter amplitude at 220 rpm. After 48 hours of incubation, the production stage was initiated by transferring 2 mL of vegetative seed to 35 mL/500 mL flask of media with the following composition: KH$_2$PO$_4$, 0.05% (w/v); K$_2$SO$_4$, 0.5% (w/v); (NH$_4$)$_2$SO$_4$, 1.0% (w/v); lactose, 12.0% (w/v), pharmamedia, 2.75% (w/v); CaCO$_3$ (precipitated), 1.0% (w/v), lard oil, 1.0% (v/v) in one liter distilled water pH 6.6. Following autoclaving, but prior to inoculation, sterile 25% sodium adipate (pH 6.6) was added to give a final sodium adipate concentration of 2.5%. Incubation, following inoculation, was then continued under the same conditions as the seed stage for 5 to 7 days.

When mycelia were needed to generate protoplasts for transformation or as a source of DNA, the strain was grown in 50 mL/250 mL flask of complete media (CM)composed of: 50 mL of 20× Cluttterbuck's salts (120 g Na$_2$NO$_3$, 10.4 g KCl, 10.4 g MgSO$_4$—7H$_2$O, 30.4 g KH$_2$PO$_4$), 2.0 mL Vogel's Trace Elements 0.3M citric acid, 0.2M ZnSO$_4$, 25 mM Fe(NH$_4$)$_2$(SO$_4$)$_2$—6$_2$O, 10 mM CuSO$_4$, 3 mM MnSO$_4$, 8 mM boric acid, 2 mM Na$_2$MoO$_4$—2H$_2$O), 5 g tryptone, 5 g yeast extract, 10 g glucose, in one liter of distilled water. Incubation was at 25° C. on a rotary shaker at 220 rpm.

EXAMPLE 2

Cephalosporium acremonium Culture Conditions

C. acremonium strains were maintained on slants containing complete medium composed of sucrose, 20 g; agar, 20 g, peptone, 4 g; yeast extract, 4 g; NaNo$_3$, 3 g; KH$_2$PO$_4$, 0.5 g; K$_2$HPO$_4$, 0.5 g; KCl, 0.5 g; MgSO$_4$/7H$_2$O, 0.5 g; FeSO$_4$/7H$_2$O, 0.01 g; in 1 liter of distilled water, pH 6.6. After ten days of growth at 28° C. and 66% relative humidity, 6 ml of sterilized water was added to the slants, and the culture growth was scraped from the agar surface. The resulting suspension was transferred to a sterile screw-top tube containing glass beads. After macerating the culture growth by vortexing for a few minutes, 3.5 ml of the resulting suspension was used to inoculate liquid cultures. This suspension was also used to provide lyophiles of the cultures for storage at 4° C. The suspension of macerated culture growth was centrifuged, the pellet resuspended in 5% skim milk, and aliquots lyophilized in sterile ampoules.

A two-stage fermentation of the strains in shake flasks was used for the production of cephalosporins or for the production of mycelia as a source of DNA and RNA. The seed stage was initiated by adding the inoculum to 250 ml flasks, each containing 15 ml of medium with the following composition: glucose, 5 g; sucrose, 40 g; corn starch, 30 g; beet molasses, 50 g; soybean meal, 65 g; CaSO$_4$/2H$_2$O, 15.8 g; ammonium acetate, 8 g; CaCO$_3$ (pptd), 5 g; (NF$_4$)$_2$SO$_4$, 7.5 g; MgSO$_4$/7H$_2$O, 3.5 g; KH$_2$PO$_4$, 1 g; soybean oil, 0.15 ml per flask in 1 liter of distilled water at pH 6.2. Incubation was at 25° C. and 65% relative humidity on a rotary shaker with a 70 mm diameter amplitude at 220 rpm. After 96 hours of incubation, the production stage was initiated by transferring 2 ml of vegetative seed to a 250 ml flask containing fresh 15 ml of the above-described media. Incubation was continued for an additional 96 hours under the same conditions.

When mycelia were needed as a source of DNA for transformation, the strains were grown in 100 ml/500 flask of complete media composed of: glycerol, 20 g; peptone 4 g: yeast extract, 4 g: KH$_2$PO$_4$, 0.5 g; K$_2$HPO$_4$, 0.5 g; KCL, 0.5 g; MgSO$_4$/7HO$_2$O, 1 g; NaNO$_3$, 3 g; FeSO$_4$/7H$_2$O, 0.01 g in 1 liter of distilled water. Incubation was at 30° C. on a rotary shaker at 200 rpm.

EXAMPLE 3

Isolation of Penicillium and Cephalosporium Genomic DNA and Total RNA

The vegetative mycelial growth from a 48 hourculture prepared as described above was collected by filtration through cheesecloth, frozen in liquid nitrogen and lyophilized overnight. The dried mycelia were ground with sand in a mortar and pestle and resuspended in 25 mL of 100 mM LiCl, 50 mM EDTA, 10 mM Tris pH 8.0, 4% SDS. After heating the suspension to 50–55° C. in a 60° C. water bath, the mixture was extracted first with 1M Tris (pH8) saturated phenol, followed by Tris-saturated phenol:chloroform (1:1, v:v) and then chloroform. RNA was precipitated from the aqueous phase by the addition of an equal volume of cold 6M LiCl and then allowing the mixture to remain at −20° C. for two to three hours. After centrifugation at 12000 xg for 20 minutes at 4° C., the supernatant was made 66% (v/v) ethanol and cooled to −20° C. for 15 minutes to precipitate the DNA. After centrifugation as described above, the DNA pellet was washed with 70% ethanol, dried and resuspended iii TE Buffer (10 mM Tris-HCl, pH7.5, 1 mM EDTA). The DNA concentration was estimated by comparison to known DNA standards when stained with ethidium bromide in agarose gel electrophoresis.

For RNA extraction, cultures of *Penicillium chrysogenum* and *Cephalosporium acremonium* as described above in Examples 1 and 2 were grown for 96 hours in 35 mL of fermentation medium (fermentation conditions previously described), at 25° C. on a rotary shaker at 220 rpm. Mycelia were collected by filtration through a Whatman #1 filter under vacuum and washed with approximately 50 mL water. The mycelia were immediately scraped from the filter, resuspended in 5 mL of "breaking buffer" (50 mM Tris-HCl pH 7.4, 150 mMNaCl, 5 mM EDTA pH 8.0, 5% SDS), frozen in liquid nitrogen and lyophilized. After overnight lyophilization, 5 mL of water containing 0.1% DEPC and 5 mL of 1M Tris (pH 8) saturated phenol:chloroform:isoamyl alcohol (50:50:1) were added and the mixture was left to thaw at 37° C. for 20 minutes with shaking. The mixture was centrifuged at 12000 xg for ten minutes at 4° C., and the aqueous layer was removed and re-extracted first with 1M Tris (pH 8) saturated phenol:chloroform:isoamyl alcohol (50:50:1), and second with 1M Tris (pH B) saturated phenol, and third with chloroform. An equal volume of 6M LiCl was combined with the final aqueous layer, and the solution was left at −20° C. for a minimum of four hours. The total RNA was pelleted at 12000 xg for 20 minutes at 4° C., the pellet dissolved in 0.3 mL TE buffer plus 0.03 mL of 3M sodium acetate, and 2.5 volumes of ethanol were added to reprecipitate the RNA. The final pellet was dissolved in 0.1 mL of TE buffer and the RNA concentration was determined spectrophotometrically using absorbance at 260 nm.

EXAMPLE 4

Construction of a *Cephalosporium acremonium* Gene Library and Isolation of the *C. acremonium* Expandase/Hydroxylase and Acetyltransferase Genes Isolation of *C. acremonium* Expandase/Hydroxylase Gene

*C. acremonium* genomic DNA was partially digested with Sau3AI to achieve an average fragment size of 10 to 20 kb and this size range was enriched by centrifugation of the digest on a 5 to 20% NaCl density gradient. The size fractionated DNA was used to create a *C. acremonium* genomic DNA library via ligation into the BamHI site of the λ 2001 vector, packaging into phage particles using Gigapak (Stratagene), and infection of *E. coli*. The resulting plaques were transferred to nitrocellulose and screened by hybridization to an oligonucleotide probe complementary to the 3' end of the published sequence of the expandase/hydroxylase gene (Samson et al., 1987). The probe was end labeled with [τ-$^{32}$P]ATP using T4 polynuleotide kinase. Positive clones were isolated, mapped for restriction endonuclease sites, and the orientation of the gene was established by Southern blot hybridization to the above oligonucleotide and another with a sequence complementary to the 5' end of the gene.

Isolation of *C. acremonium* Acetyltransferase Gene

Although it was not the procedure used in the isolation of the acetyltransferase gene for the subsequent vector constructions described below in Examples 11 and 12, the following procedure could be used by one of ordinary skill using published DNA sequence information currently available. From a *C. acremonium* genomic library constructed as described above, a clone is selected which encodes the acetyltransferase gene based on hybridization to synthetic oligonucleotide probes complimentary to the acetyltransferase sequence, as described in Matsuda et al. (1992) *Biochem. Biophys. Res. Commun.* 182:995–1001.

EXAMPLE 5

*Streptomyces clavuligerus* Culture Conditions

The *Streptomyces clavuligerus* strain used in these procedures was ATCC 27064. The strain was maintained on plates consisting of: yeast extract, 4 g; malt extract, 10 g; glucose, 4 g; agar, 20 g; in one liter of distilled water, pH 7.2. After 5 days of growth at 30° C., 2 mL of sterile water was added to the plates and the culture growth was scraped from the agar surface. The resulting suspension was transferred to a sterile screw-top tube containing glass beads. After macerating the culture growth by vortexing, the suspension was used to inoculate liquid cultures. The suspension was also used forpermanent culture storage at −70° C. by adding glycerol to 15% final volume.

When mycelia were needed to generate protoplasts for transformation or for a source of DNA, the strains were grown in 200 mL/1 liter flask of YEME media composed of: yeast extract 3 g; peptone, 5 g: malt extract, 3 g; glucose, log; sucrose, 340 g; $MgCl_2$—$6H_2O$, 1.02 g; glycine, 5 g; agar, 18 g; in one liter of distilled water. Incubation was at 28° C. on a rotary shaker at 220 rpm.

EXAMPLE 6

Isolation of Streptomyces Genomic DNA

The vegetative growth from a 48 hour culture prepared as described above was collected by centrifugation at 22100 xg for 10 minutes. The cells were resuspended in 10 mL of TE buffer and 10 mg of lysozyme was added and the mixture was incubated at 30° C. for 15 minutes. One mL of 20% SDS was then added, immediately followed by 10 mL of TE (pH 8) saturated phenol and 1.5 mL of 5M NaCl and the mixture was inverted gently for 20 minutes. The phases were separated at 12000 xg for 10 minute after which the aqueous layer was removed and transferred to a fresh tube. An equal volume of chloroform was added and the mixture was inverted gently for 10 minutes. The phases were separated again by centrifugation at 12000 xg for 10 minutes and the aqueous layer removed and again transferred to a fresh tube. Two volumes of isopropanol werecarefully added and the precipitated DNA was spooled and redissolved in a minimum volume of TE buffer. RNAse A was added to a final concentration of 20 µg/mL and the solution was incubated at 50° C. for one hour. Protease K was then added to a final concentration of 100 µg/mL, along with 100 mM NaCl and 0.4% SDS, and the mixture was incubated at 37° C. for one hour. The solution was extracted again with an equal volume of TE (pH 8) saturated phenol, followed by another chloroform extraction. The DNA from the final extraction was spooled after addition of two volumes of isopropanol and the concentration was determined spectrophotometrically using an absorbance reading at 260 nm.

EXAMPLE 7

Construction of a Gene Library and Isolation of DNA Fragments Containing the *Streptomyces clavuligerus* Expandase and Hydroxylase Genes Isolation of the *S. clavuligerus* Expandase Gene

*Streptomyces clavuligerus* genomic DNA obtained from the procedure previously described was digested with the restriction enzymes Bam HI and Sal I. The digested DNA was electrophoresed on a 0.8% agarose gel and 1.8 to 2.2 kb sized fragments were eluted and ligated to pUC18 DNA which had been previously digested with Bam HI and Sal I. Dilutions of the ligation mixture were used to transform competent JM109 cells using electroporation (Gene Pulser, Bio-Rad, Richmond, Calif.). Preparation of the competent-cells and electroporation conditions were both according to the manufacturer's recommendations. The transformation mix was plated onto LB plates containing 100 µg/mL ampicillin, and 75 µL of 2% X-Gal. Following overnight incubation at 37° C., recombinant colonies were identified by their colorless appearance due to inactivation of the plasmid vector beta-galactosidase gene activity. The colorless colonies were picked to a fresh LB plate containing 100 µg/mL ampicillin. After overnight growth at 37° C. the colonies were transferred to nitrocellulose and hybridized with a probe produced by polymerase chain reaction which corresponded to the published *Streptomyces clavuligerus* expandase gene sequence from bases 52–918 [Kovacevic et al, (1989) *J. Bacteriol.* 171:754–760; and Ingolia et al. U.S. Pat. No. 5,070,020]. Labelling of the polymerase chain reaction product was accomplished by random-primer extension reaction with ($^{32}$P) dCTP and an Oligolabelling Kit, per the manufacturer's instructions (Pharmacia, Piscataway, N.J.). The hybridization reaction was performed in the presence of $10^6$ CPM of radiolabeled probe, 30% formamide, 5× SSC (0.15M NaCl, 0.015M sodium citrate pH7), 0.1% SDS, 5× Denhardt's (5 g ficoll, 5 g polyvinylpyrolidone, and 5 gBSA for 500 mL of 50× stock) and 100 µg/mL calf thymus DNA, at 37° C. overnight. Several transformants hybridized strongly to the probe. One colony was confirmed to contain a vector carrying the expandase gene by restriction enzyme analysis and this plasmid was designated pFTSO-1.

Isolation of the *S. clavuligerus* Hydroxylase Gene

*Streptomyces clavuligerus* genomic DNA was partially digested with BamHI and ligated into the lambda Dash II vector from Stratagene. The resulting genomic library was screened by hybridization to a 30 base oligonucleotide having the identical sequence as the first 30 bases of the published sequence for the hydroxylase gene (Kovacevic and Miller, 1991, *J. Bact.* 173:398). Southern hybridization with BamHI digested DNA from two positive phage clones revealed the expected 6 kb fragment, which was subcloned. This subclone yielded a set of fragments after digestion with KpnI in agreement with the published restriction map for the region around the hydroxylase gene (Kovacevic and Miller, 1991).

EXAMPLE 8

Isolation of Plasmid DNA

*E. coli* cultures containing the plasmid of interest were grown in 500 mL LB broth (20 g/l of LB Broth Base (Gibco, Paisley, Scotland), with 15 µg/mL tetracycline on a rotary shaker at 220 rpm for 12–16 hours at 37° C. The cells were pelleted by centrifugation at 4000 xg for ten minutes at 4° C. The cell pellet was resuspended in 18 mL Glucose Buffer (50 mM glucose, 25 mM Tris pH8.0, 10 mM EDTA) and 2 mL of 40 mg/mL lysozyme (Sigma, St. Louis, Mo.) in glucose buffer was added, mixed, and the mixture was incubated at room temperature for 15 minutes. Forty mL of a freshly prepared solution of 0.2N NaOH, 1% SDS was added, and the mixture swirled gently andplaced on ice for ten minutes. Thirty mL of 5M potassium acetate pH 4.8 were then added, mixed well, and the resultant mixture was placed on ice for an additional ten minutes. The cellular debris were pelleted by centrifugation at 4000 xg for ten minutes at 4° C. and the resulting supernatant was filtered through a cheesecloth filter. Isopropanol (0.6 volumes) was added to the clarified supernatant to precipitate the plasmid DNA, and the precipitate was formed during incubation at room temperature for 20 minutes. The plasmid DNA was pelleted at 4000 xg for 20 minutes at 4° C. and then washed with 70% ethanol and dried briefly. The pellet was resuspended in 9 mL TE buffer, then 10 grams of CsCl and 0.387 mL of a 10 mg/mL ethidium bromide solution were added. This solution was centrifuged at 313,100 xg for 24 hours. The resulting plasmid band in the cesium chloride gradient was visualized with ultraviolet light, isolated, and then the ethidium bromide was removed using water saturated butanol for extraction. The CsCl in the plasmid preparation was then removed by dialysis against TE buffer, and finally the DNA was concentrated using PEG (MW 8000). Concentration of DNA was determined spectrophotometrically using an absorbance reading at 260 nm.

EXAMPLE 9

Construction of the Penicillium Transformation Vector pPenFTSO

Incorporation of the Phleomycin Resistance Gene

A Penicillium transformation vector was constructed with a phleomycin resistant gene as a dominate selectable marker. This was accomplished first by isolating a 660 bp fragment, containing the phleomycin resistance gene (a phleomycin binding protein gene from *Streptoalloteichus hindustanus*) and also coupled to a yeast cytochrome C1 terminator, from a Bam HI/Bgl II digest of plasmid pUT713 (CAYLA, Toulouse Cedex, France) by electrophoresis on and elution from agarose gels. The isolated fragment was ligated into the Bam HI site of vector PSELECT® 1 (Promega Corporation) and the orientation of the gene was determined by restriction enzyme analysis. The unique HindIII site in the resulting plasmid was removed by restricting with HindIII, filling in with Klenow polymerase and religating. Next, a 550 bp Pst I fragment, containing the lambda cos site was inserted which enables the vector to be used for cosmid formation when appropriate size inserts are included. This vector is designated pSCP4.

*P. chrysogenum* genomic DNA wits partially digested with Sau3A and used to prepare a library in the phage vector lambda EMBL3. A clone containing the isopenicillin N synthetase (IPNS) gene was isolated from this library and used to prepare a series of subclones, one of which contained a 3.6 kb fragmentfrom the first BamHI site upstream of the IPNS gene to the first HindIII site downstream of the gene. The unique SalI site in this subclone was removed by restricting with SalI, filling in the recessed ends with Klenow polymerase and religating. Next, the unique XbaI site was removed similarly by restricting with XbaI, filling in and religating. The resulting plasmid is designated pSXF-1. The engineered IPNS promoter was gel isolated from PSXF-1 as a 1.2 kb NcoI fragment and ligated into the NcoI site of pSCP4, described above. The orientation, determined by restriction digestion, was chosen so that the promoter was fused to the phleomycin resistance gene at the ATG start codon. This plasmid is designated pUTZ-2.

Incorporation of the *S. clavuligerus* Expandase Gene

The 1.645 kb fragment containing the *Streptomyces clavuligerus* expandase gene was purified from a Bam HI and Sal I digest of the pFTSO-1 (vector previously described) by electrophoresis on and elution from a 0.8% agarose gel. The isolated fragment was ligated into vector pSELECT (Promega Corporation) also digested with Bam HI and Sal I. This vector was designated pFTSO-8. A novel Nco I site was created at the ATG start codon of the expandase gene by site-directed mutagenesis of pFTSO-8 using the Altered Sites® in vitro Mutagenesis System (Promega Corporation). Mutagenesis was performed per the manufacturer's instructions. An oligonucleotide was constructed to complement the coding sequence of the DNA region at the ATG start codon from thepublished sequence of the Streptomyces expandase gene (Kovacevic et al, (1990) Journal of Bacteriology, 171, p. 3952–3958). The oligonucleotide was synthesized by cyanoethyl phosphoramidite chemistry (Pharmacia Gene Assembler instrumentation), and the oligo sequence was as follows:

SEQ ID NO:8
   3'   CGAGAGGATCAGTGAGAGTCCATGGACACGACGG 5'.

The mutagenesis was confirmed by restriction enzyme analysis. Next, the 1.2 kb NcoI fragment from pUTZ-2, containing the engineered *P. chrysogenum* IPNS promoter region, was isolated by restriction with NcoI, followed by agarose gel electrophoresis. The IPNS-promoter region was ligated into the pFTSO-8 vector at the novel Nco I site created by the mutagenesis at the ATG start codon of the expandase gene. Orientation of the promoter to the expandase gene was established by restriction enzyme analysis. This IPNS-promoter:expandase gene cassette was then removed as a Bam HI/Sal I fragment: into the Bam HI/Sal I cut Penicillium transformation vector pUTZ-2 described above. The final construction was designated pPenFTSO.

EXAMPLE 10

Construction of the Penicillium Transformation Vector pPEN/CEPH-1

Incorporation of the IPNS Promoter Region

The IPNS promoter region was isolated from pUTZ-2 described further above in Example 9, by digestion with Xho I/Sma I. The pUTZ-2 vector was cut with Bam HI and the protruding ends were filled in using dNTP's and Klenow fragment, creating blunt ends, and then digested with Xho I and the isolated Xho I/Sma IIPNS promoter fragment was ligated into this cut vector resulting in a construct which contained two IPNS promoter regions. This vector was designated pUTZ-7.

Incorporation of the *C. acremonium* Expandase/Hydroxylase Gene

One of the IPNS promoter regions was then isolated (by electrophoresis on and elution from agarose gels) from pUTZ-7 as a Xho I/Xba I fragment and ligated into the Xho I/Xba I cut vector pBluescript II SK (Stratagene, La Jolla, Calif.). This vector was designated pIPNSp/blue.

The Cephalosporium expandase/hydroxylase gene was isolated (by electrophoresis on and elution from agarose gels) as a 1.6 kb Hind III/Xba I fragment from one such genomic clone identified above and ligated into a Hind III/Xba I digested vector pSELECT. A novel Bsp HI site was created at the ATG start codon of the expandase/hydroxylase gene by site-directed mutagenesis using the Altered Sites™ in vitro Mutagenesis System (Promega Corporation). Mutagenesis was performed per the manufacturer's instructions. An oligonucleotide was constructed to complement the coding sequence of the DNA region at the ATG start codon from the published sequence of the *Cephalosporium acremonium* expandase/hydroxylase gene (Samson et al., *Bio/Technology*, Vol.5, November, 1987). The oligonucleotide was synthesized by cyanoethyl phosphoramidite chemistry (Pharmacia Gene Assembler instrumentation), and the oligo sequence was as follows:

SEQ ID NO:9    3'   GTTTTGGTGTCGTAGTAG-TACTGAAGGTTCCAG 5'.

The mutagenesis was confirmed by restriction enzyme analysis. The *Cephalosporium acremonium* expandase/hydroxylase gene was then isolated (by electrophoresis on and elution from agarose gels) as a Bsp HI/Xba I fragment and ligated into the Nco I/Xba I digested vector pIPNSp/blue described in the Example above. This vector now contained the Penicillium IPNS promoter at the ATG of the *Cephalosporium acremonium* expandase/hydroxylase gene. This vector was designated pIPNSp/EXP/blue. This IPNS promoter:expandase/hydroxylase cassette was partially digested with Xho I and completely digested with Xba I and the fragment isolated (by electrophoresis by and elution from agarose gels), and ligated into a Xho I/Xba I digested vector pUTZ-2 described in the Example above, to yield the final transformation vector pPEN/CEPH-1.

EXAMPLE 11

Construction of a Penicillium Transformation Vector to Express Both the Expandase and Hydroxylase Genes of *S. clavuligerus*

The *P. chrysogenum* β-tubulin gene was cloned from a lambda genomic library using the *Aspergillus niger* β-tubulin gene as a hybridization probe. A 2.0 kb XbaI/HindIII fragment containing the Penicillium β-tubulin promoter was ligated into the XbaI/HindIII sites of pSELECT (Promega). An NcoI site was introduced at the ATG start codon by site-directed mutagenesis of the sequence AAAATGCGT to ACCATGGGT. From the resulting vector, a 1.4 kb BamHI/NcoI fragment was gel isolated and ligated between the BamHI and NcoI sites of pUTZ-2 ((described previously) to generate the vector pCI-6. From a *P. chrysogenum* genomic clone, a 5.1 kb SalI fragment containing both the IPNS and acyl transferase genes was gel isolated and ligated into the SalI site of pUTZ-2 to create pUTZ-5. The 3' terminator sequence of the IPNS gene was isolated from pUTZ-5 by restriction with BamHI and HindIII followed by gel isolation of the 1.3 kb fragment, which was ligated between the BamHI and HindIII sites of pCI-6 (described above) to give pCI-13. The unique SalI site near the BamHI site in pCI-13 was removed by restriction, fill-in with Klenow polymerase and religation. A new SalI site was introduced on the other side of the BamHI site by site-directed mutagenesis of the sequence GGAAGACG to GGTCGACG. The ampicillin resistance gene was then removed from the plasmid by restricting with PvuI, gel isolating the larger fragment, and religating to give pCI-15. Finally, the IPNS promoter:expandase gene cassette was gel isolated from pPENFTSO as a 2.4 kb BamHI/SalI fragment and ligated into pCI-15 to give pEXP-1.

Construction of a vector for expressing both the hydroxylase and expandase genes of *S. clavuligerus*, involves the following steps. The 2.9 kb KpnI fragment containing the hydroxylase gene is subcloned into pSELECT so that the EcoRI site in the polylinker is next to the 5' end of the gene. The unique NcoI site within the plasmid is removed by site-directed mutagenesis of the sequence TCCATGGGC to the sequence TCGATGGGC, and simultaneously, a new NcoI site is introduced at the start codon by changing the sequence AACATGGC to ACCATGGC. Both changes preserve the encoded amino acid sequence. The 1.0 kb EcoRI/NcoI fragment containing the engineered IPNS promoter is gel isolated from pUTZ-2 and ligated between the EcoRI and NcoI sites of the above vector containing the altered hydroxylase gene. Next, the unique EcoRI site in the resulting vector is changed to a HindIII site by site-directed mutagenesis. The 5'IPNS:hydroxylase fusion construct is isolated from the resulting vector as a HindIII fragment, which is then ligated into the unique HindIII site of the vector pEXP-1 described above. The final vector contains the expandase and hydroxylase genes each driven by the IPNS promoter, and the phleomycin resistance marker driven by the β-tubulin promoter.

EXAMPLE 12

Construction of the Penicillium Transformation Vector pPenCACT

Incorporation of the Hygromycin Resistance Gene

A Penicillium transformation vector was constructed with a hygromycin resistant gene as the dominate selectable marker. The *E. coli* hygromycin B phosphotransferase gene was isolated (by electrophoresis on and elution from agarose gels) as a 1.15 kb Bam HI fragment from vector pHph-1 (Boehringer Mannheim, Indianapolis, Ind.) and ligated to Bam HI digested vector mpl9. The orientation of the hygromycin resistance gene in mpl9 was determined from restriction enzyme analysis of RF DNA. The 5' Bam HI site is near the ATG stare codon of the hygromycin resistance gene. To facilitate positioning of an alternate promoter at this 5' BamHI site the 3' Bam HI site was removed by site-directed mutagenesis using the Mutator™ Site Directed Mutagenesis Kit (Stratagene, La Jolle, Calif.). Mutagenesis was performed per the manufacturer's instructions. An oligonucleotide was constructed to complement the DNA region at the 3' Bam HI site from the published sequence of the *E. coli* hygromycin B phosphotransferase gene (Gritz, L. and Davies, J., 1983, Gene 25, 179). The oligonucleotide was synthesized by cyanoethyl phosphoramidite chemistry (Pharmacia Gene Assembler instrumentation), and the oligo sequence was as follows:

```
SEQ ID NO:10
    5'   TACCCGGGGTTCCCGCGAACT  3'.
```

The mutagenesis was confirmed by restriction enzyme analysis. The mutagenized hygromycin resistance gene was then isolated as a Sma I/Xba I fragment (by electrophoresis on and elution from agarose gels) and ligated into Sma I/Xba I digested vector pUC 18.

The Penicillium IPNS promoter was isolated (by electrophoresis on and elution from agarose gels) as a 1.2 kb Nco I fragment from the Nco I cut vector pUTZ-2 (vector previously described). Synthetic oligonucleotide linkers were synthesized to create a Bam HI site from the Nco I sites on the ends of the IPNS promoter fragment so as to position the IPNS promoter in the 5' Bam HI site near the ATG of the hygromycin resistance gene. The oligos were synthesized by cyanoethyl phosphoramidite chemistry (Pharmacia Gene Assembler instrumentation), and theoligo's sequences are as follows:

```
SEQ ID NO:11
    5'   CATGAAGAAG   3'

SEQ ID NO:12
              3'   TTCTTCCTAG  5'.
```

This sequence retains the native sequence of the IPNS promoter but inserts two amino acids in the hygromycin resistance gene. The oligos were annealled, phosphorylated and ligated to the Nco I cut IPNS promoter fragment resulting in Bam HI sites at both the 5' and 3' ends of the IPNS promoter fragment. This linkered promoter was ligated to Bam HI cut hygromycin resistance gene in pUC 18, and the orientation was confirmed by restriction enzyme analysis. This IPNS promoter:hygromycin resistance gene cassette was then isolated (by electrophoresis on and elution from agarose gels) as a 2.1 kb Xho I/Sal I (Xho I site is located at the 5' end of the IPNS promoter, and the Sal I site is from the pUC polylinker and ligated into Sal I digested vector pSELECT. The orientation of the cassette was determined by restriction enzyme analysis. This vector was designated pIPNS/HYG.

Incorporation of *Cephalosporium acremonium* Acetyltransferase Gene

The Cephalosporium acetyltransferase gene was isolated from a genomic clone (described above) as a 1.8 kb Bgl II/Sal I fragment by electrophoresis on and elution from agarose gels. The acetyltransferase gene was ligated into the Bam HI/Sal I digested vector pSELECT. To facilitate positioning of the Penicillium IPNS promoter at the ATG of the Cephalosporium acetyltransferase gene, a novel Nco I site was created at the ATG of the acetyltransferase gene, and an internal Nco I site in the structural gene was removed by site-directed mutagenesis using the Altered Sites™ in vitro Mutagenesis System (Promega Corporation). Mutagenesis was performed per the manufacturer's instructions. The oligonucleotides were constructed to complement the coding sequence of the DNA regions of interest from the sequence of the Cephalosporium acetyltransferase gene set out above in SEQ ID NO:1 and 2. The oligonucleotide sequence used to remove the internal Nco I site in the structural gene was as follows:

```
SEQ ID NO:13
    3'   GTCGGCGCATCGATGGGTGGAAT  5'.
```

The oligonucleotide sequence used to create the novel Nco I site at the ATG start codon was as follows:

```
SEQ ID NO:14
    3'   CGCCCACCATGGCGCCTCAGAT  5'.
```

These oligonucleotides were synthesized by cyanoethyl phosphoramidite chemistry (Pharmacia Gene Assembler instrumentation). Mutagenesis was confirmed by restriction enzyme analysis. This vector was designated pMUTACT.

The Penicillium IPNS promoter was isolated (by electrophoresis on and elution from agarose gels) as a 1.2 kb Nco I fragment from vector pUTZ-2 described in an Example further above. This promoter fragment was ligated to Nco I cut vector pMUTACT which now positioned the IPNS promoter directly at the ATG of the *Cephalosporium acremonium* acetyltransferase gene. Orientation of the promoter was confirmed by restriction enzyme analysis. This IPNS promoter:acetyltransferase gene cassette was digested with Xho I/Sal I (Xho I site is located at the 5' end of the IPNS promoter and Sal I site is at the 3' end of the acetytransferase gene) and ligated into Sal I digested vector pSELECT. The orientation of the fragment was determined by restriction enzyme analysis. This vector was designated pMUTACT/IPNS.

The mutagenesis used to create the novel Nco I site at the ATG of the acetyltransferase gene resulted in a change in the second amino acid from a serine to an alanine. In order to keep the coding sequence identical to the native gene, a site-directed mutagenesis was done using the Altered Sites™ in vitro Mutagenesis System. The oligonucleotide was constructed to complement the coding sequence of the DNA region of interest from the sequence of the acetyltransferase gene set out above as SEQ ID NO: 1 and 2. The oligonucleotide sequence used to change the second amino acid from an alanine to a serine was as follows:

```
SEQ ID NO:15
    3'   TCTAGCTAGACACCATGTCGCCTCAGAT  5'.
```

The oligonucleotide was synthesized using cyanoethyl phosporamidite chemistry (Pharmacia Gene Assembler instrumentation). The mutagenesis was confirmed by DNA sequencing using the USB Sequenase Version 2.0 DNA Sequencing Kit (USB, Cleveland, Ohio). Sequencing primers were synthesized using cyanoethyl phosphoramidite chemistry (Pharmacia Gene Assembler instrumentation). This vector was designated pMUTACT/IPNS-2.

The IPNS promoter:hygromycin resistance gene cassette was removed from vector pIPNS/HYG as a Xba I fragment and ligated into Xba I digested vector pMUTACT/IPNS-2 to give the final transformation vector pPenCACT. The orientation of the hygromycin cassette was determined by restriction enzyme analysis.

EXAMPLE 13

Construction of a Penicillium Transformation Vector pTS-8 to Express both the Expandase/Hydroxylase and Acetyltransferase Genes of *Cephalosporium acremonium*

The Cephalosporium acetyltransferase gene was isolated (by electrophoresis on and elution from agarose gels) as 1.8 kb Bgl II/Sal I fragment from a genomic clone and ligated into a Bam HI/Sal I digested vector pSELECT (Promega Corporation). To facilitate positioning of the Penicillium IPNS promoter at an ATG of the Cephalosporium acetyltransferase gene, a novel Nco I site was created at an ATG codon located at base −42 (Mathison et al., *Current Genetics*, submitted) and an internal Nco I site in the structural gene was removed by site-directed mutagenesis using the Altered Sites in vitro Mutagenesis System (Promega Corporation). Mutagenesis was performed per the manufacturer's instructions. The oligonucleotides were constructed to be complementary to the coding sequence of the DNA regions of interest, but which incorporated several changes to create or remove an Nco I site. The oligonucleotide sequence used to remove the internal Nco I site in the structural gene was as follows:

```
SEQ ID NO:16
    3'    GTCGGCGCATCGATGGGTGGAAT 5'.
```

The oligonucleotide sequence used to create the novel Nco I site at the ATG at base −42 was as follows:

```
SEQ. ID NO:17
    5'    CTCCGATAGGGCGTGGTACCCGGCCCTACTCTTAT 3'.
```

The oligonucleotides were synthesized by cyanoethyl phosphoramidite chemistry (Pharmacia Gene Assembler instrumentation). Both mutagenesis events were confirmed by restriction enzyme analysis. This vector was designated pMUTACT. The Penicillium IPNS promoter was isolated (by electrophoresis on and elution from agarose gels) as a 1.2 kb Nco I fragment from vector pUTZ-2 previously described further above. This promoter fragment was ligated to Nco I cut vector pMUTACT which now positioned the IPNS promoter directly at the −42 ATG of the Cephalosporium acetyltransferase gene. Orientation of the promoter was confirmed by restriction enzyme analysis. This vector was designated pMUTACT/IPNS. A 2.5 kb Xho I/Sal I fragment was isolated (by electrophoresis on and elution from agarose gels) from vector pMUTACT/IPNS which contained the IPNS promoter:acetyltransferase cassette and ligated to a Sal I digested vector pUTZ-2 (previously described). This intermediate vector was then digested with Xba I and ligated with a 2.1 kb Xba I fragment from vector pPEN/CEPH-1 (previously described) containing the IPNS promoter:expandase/hydroxylase cassette to yield the final transformation vector pTS-8.

EXAMPLE 14

Transformation of *Penicillium chrysogenum*

Protoplasts from the *Penicillium chrysogenum* strain described above were generated by inoculating 50 mL of CM broth with 1×10⁷ spores for 67 hours at 25° C. on a rotary shaker at 220 rpm. The mycelia were collected by filtration onto cheesecloth filters, transferred to 500 mL flasks and resuspended in 25 mL KMP (0.7M KCl, 0.8M mannitol, 0.02KPO$_4$ pH6.3), containing 100 mg Novozyme 234 (Novo BioLabs, Bagsvaerd, Denmark) and allowed to incubate at 30° C. at 100 rpm. The spheroplasts were separated by filtration through cheesecloth/glasswool filters and pelleted by centrifugation at 350 xg for 10 minutes. The spheroplasts were then washed three times with 10 mL of KMP buffer, and then resuspended in KMPC (KMP with 50 mM CaCl$_2$) to a concentration of 5×10⁷ cells/mL and left at room temperature for 20 minutes. For transformation of the Penicillium, 200 μl of the spheroplast suspension was added to DNA (5 μg vector DNA in 6.2 μl of KMPC with 5 mg/mL heparin) along with 50 μl of PPC (40% PEG MW 3500, 20 mM KPO$_4$, pH 6.3, 5% CaCl$_2$ was added just before use) and the transformation mix was incubated on ice for 30 minutes. One mL of freshly prepared PPC was added and the mixture was transferred to 50 mL of molten (50° C.) regeneration agar (CM plus 1.3M mannitol and 3% agar). The transformation mixture was then distributed between 5 petri dishes. After regeneration for 24 hours at 25° C. the plates were then overlayed with OL (1% peptone in 1% agar) containing 100 μg/50 mL OL of phleomycin. The amount of overlay was equal to the amount of regeneration agar. The plates were incubated at 25° C. for 7–14 days and observed for generation of transformant colonies.

EXAMPLE 15

Bioactivity Assays

An agar diffusion bioassay was used to determine antibiotic activity of the HPLC isolated adipoyl-6-APA and the adipoyl-7-ADCA fermentation products. Twenty μL of isolated product was applied to 5 mm discs on an LB agar plate (20 g/L of LB Broth Base with 3% agar (Gibco, Paisley, Scotland) seeded with *Bacillus subtilus* ATCC 33677, or *E. coli* Super Sensitive strain (supplied by Prof. Arnold L. Demain, MIT). Bacillus subtilus was used as the indicator strain to assay the adipoyl-6-APA product and the *E. coli* Super Sensitive strain was used as the indicator strain to assay the adipoyl-7-ADCA product. After 15 hours of incubation at 37° C. a halo of inhibited growth of the indicator bacteria around the disk indicated the products showed bioactivity. The controls in this experiment included deacetoxycephalosporin C, cephalosporin C, penicillin V, and agar containing penicillinase or no penicillinase as is lo a control for confirmation of β-lactam structures.

EXAMPLE 16

HPLC Method for Simultaneous Analysis of adipoyl-: 6-APA, 7-ADCA, 7-ADAC and 7-ACA Fermentation products from transformed Penicillium strains (adipoyl-6APA, adipoyl-7-ADCA, adipoyl-ADAC and adipoyl-7-ACA) were simultaneously analyzed by high performance liquid chromatography (HPLC). The HPLC system consisted of the following Waters components: 625 solvent delivery system, 409E variable wavelength detector (set at 220 nm and 260 nm), 825 Maxima data system. The stationary phasewas a Nova-Par $C_{18}$ 5×100 mm radial compression cartridge with a Nova-Pak $C_{18}$ Guard-Pak insert. The mobile phase (at 1 ml/min flow) consisted of a 10 min linear gradient from the initial conditions of 5% methanol and 95% 10 mM $KPO_4$, pH 5 to 40% methanol and 60% $KPO_4$, pH 5. Adipoyl-6-APA was quantitated by comparison to a standard curve of penicillin N at 220 nm. The expanded products were(quantitated by comparison to standard curves at 260 nm of synthetic adipoyl-7ADCA and adipoyl-7-ACA.

EXAMPLE 17

RAEV Enzyme Assays

Chemically synthesized adipoyl-7-ADCA and adipoyl-7-ACA were used as substrates to determine the specific activity of the RAEV enzyme (commercially available from RAEV Corp.). The reaction mix contained 10 mM substrate, 1 μg RAEV enzyme, 5% glycerol, in 0.16M $KH_2PO_4$ in a total volume of 50 μl, and was incubated at 37° C. (More optimal reaction conditions include the use of 20 mM or greater of substrate in 20–50 mM of potassium phosphate buffer.) Five μl aliquots were taken at time points 0, 1, 3, 5, 10, 20, end 30 minutes, diluted with 35 μl of 0.010M $KH_2PO_4$ pH 3.5, and frozen at −70° C. before analysis lay HPLC under conditions previously described.

Activity of the RAEV enzyme against a calorimetric adipoyl-P-aminobenzoic acid substrate was assayed using 5 mM substrate, 8.25 μg RAEV enzyme, 10% glycerol, in 0.065M $KH_2PO_4$ pH 7.0, ina total volume of 50 μl for 30 minutes at 37° C. The reaction was carried out in a 96 well microtiter dish. Fifty μl of a 1/100 dilution of 1M $NaNO_2$ in 0.25M acetic acid was added to terminate the reaction and the reaction was left at room temperature for 3 minutes. One hundred μl of a 1/100 dilution of 10 mg/mL 4-amino-5-hydroxy-2,7-naphthalene-disulfonic acid, monosodium salt hydrate in $H_2O$ into 0.5M $NaCO_3$ was added and the color development was monitored immediately at 515 nm using a EL 312 Bio-kinetics Plate Reader (BioTek Instruments).

EXAMPLE 18

Assessment of Alternative Adipoyl Acylases

In addition to the studies using the RAEV enzyme, the removal of the adipoyl side chain from adiployl-7-ADCA (and other adipoyl compounds) was demonstrated with enzymes produced from a variety of microbial sources. In an initial study the Asahi Pseudomonas sp. strains SE-83 and SE-495 (deposited with the Fermentation Research Institute under the accession numbers FERM BP-817 and FERM BP-818, respectively) and the Toyo Jozo Pseudomonas strain SY-77-1 (deposited with the Northern Regional Research Laboratory under the accession number NRRL B-8070) were grown for 72 hours in a medium containing HyCase SF, 2.0% (w/v); monosodium glutamate, 0.5% (w/v); yeast extract, 0.5% (w/v); corn steep powder, 0.2% (w/v); cotton seed oil, 0.5% (w/v) and glutaric acid, 0.1% (w/v). Cells were harvested by centrifugation and washed with 50 mM phosphate buffer, pH 8.0; they were then resuspended in buffer and the outer membranes made permeable by the addition of a small volume of chloroform. Aliquots of cell suspension were then mixed with adipoyl-para-nitroanilide (ad-pNA) and incubated at 30° C. for periods of 2 to 18 hours. Following incubation, the mixtures were acidified by the addition of 10% (v/v) acetic acid. Liberated p-nitroaniline was then detected by calorimetric means following its conversion to a diazo compound utilizing the reagents supplied in kit-form by Sigma Chemical Company for the assay of gamma-glutamyl-transferase (Sigma product number 545-A). The relative activities of the three strains were 100%, 85.5% and 48% for SE-495, SE-83 and SY-77-1 respectively. Using methods similar to those described for the RAEV enzyme above, activity of the SE-83 and SE-495 enzymes on adipoyl-7-ADCA was also demonstrated. The production of beta-lactamase by SY-77-1 prevented the demonstration of deacylating activity by this strain on adipoyl-7-ADCA.

By similar means adipoyl-acylase production was also demonstrated for two fungal strains (Alternaria sp. MA-133, ATCC No. 20492 and Aspergillus sp. MA-13, ATCC No. 20491; ref. U.S. Pat. No. 4,141,790 to Meiji Seika Kaisha Ltd.) and three additional bacterial strains (a Brevibacterium, ATCC No. 14,649, a Achromobacterium, ATCC No. 14,648, and a Flavobacterium, ATCC No. 14,650, which were described as cephalosporin C acylase producers in U.S. Pat. No. 3,239,394 to Merck & Co., Inc.)

What is claimed is:

1. A bioprocess for preparing adipoyl-7-ACA comprising the steps of:
   (a) transforming cells of a strain of *Penicillium chrysogenum* which produces isopenicillin N with an expression vector containing DNA encoding an enzyme, having expandase activity capable of accepting adipoyl 6-APA as a substrate, an enzyme having hydroxylase activity capable of accepting adipoyl-7-ADCA as a substrate and an enzyme having acetyltransferase activity capable of accepting adipoyl 7-ADAC as a substrate;
   (b) culturing the transformed cells from step a) in a suitable culture medium containing an adipate feedstock, wherein said cells produce adipoyl-6-APA; and
   (c) culturing the transformed cells producing adipoyl-6-APA of step b) under conditions suitable for expression of said DNA encoding enzyme, thereby producing the end product adipoyl-7-ACA.

2. A bioprocess according to claim 1 wherein said DNA encoding said expandase and hydroxylase activity is obtained from *Cephalosporium acremonium*.

3. A bioprocess according to claim 1 wherein said DNA encoding said acetyltransferase activity is obtained from *Streptomyces clavuligerus*.

* * * * *